(12) United States Patent
Dearden et al.

(10) Patent No.: US 12,042,164 B2
(45) Date of Patent: Jul. 23, 2024

(54) JOINT ASSEMBLIES WITH CROSS-AXIS FLEXURAL PIVOTS

(71) Applicant: Intuitive Surgical Operations, Inc., Sunnyvale, CA (US)

(72) Inventors: Jason Dearden, Provo, UT (US); Clayton Grames, Santa Clara, CA (US); Larry L. Howell, Orem, UT (US); Brian D. Jensen, Orem, UT (US); Spencer P. Magleby, Provo, UT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 17/856,189

(22) Filed: Jul. 1, 2022

(65) Prior Publication Data

US 2022/0330967 A1    Oct. 20, 2022

Related U.S. Application Data

(63) Continuation of application No. 16/332,515, filed as application No. PCT/US2017/051276 on Sep. 13, 2017, now Pat. No. 11,432,836.
(Continued)

(51) Int. Cl.
*A61B 17/29* (2006.01)
*A61B 17/00* (2006.01)
(Continued)

(52) U.S. Cl.
CPC .......... *A61B 17/29* (2013.01); *B25J 15/0233* (2013.01); *A61B 2017/00309* (2013.01);
(Continued)

(58) Field of Classification Search
CPC .......... A61M 25/0147; A61M 25/0054; A61M 25/0138; A61M 25/0141;
(Continued)

(56) References Cited

U.S. PATENT DOCUMENTS 3,140,614 A    7/1964   James et al.
3,482,466 A    12/1969  Orlich et al.
(Continued)

FOREIGN PATENT DOCUMENTS

CN    2626684 Y    7/2004
CN    101534751 A  9/2009
(Continued)

OTHER PUBLICATIONS

Office Action for CN Application No. 2017800695977, mailed Aug. 29, 2022, 9 pages.
(Continued)

*Primary Examiner* — Majid Jamialahmadi

(57) ABSTRACT

The embodiments described herein can be used in a variety of grasping, cutting, and manipulating operations. In some embodiments, an apparatus includes a first joint member, a second joint member, and a flexure. The first joint member includes a first connection portion and a contact surface. The second joint member including a second connection portion. A first end portion of the flexure is coupled to the first connection portion, and a second end portion of the flexure is coupled to the second connection portion. The flexure is configured to deform elastically when the first joint member and the second joint member move from a first configuration to a second configuration. When in the first configuration, the central portion of the flexure is spaced apart from the contact portion. When in the second configuration, the central portion of the flexure contacting the contact portion.

9 Claims, 28 Drawing Sheets

Related U.S. Application Data

(60) Provisional application No. 62/394,310, filed on Sep. 14, 2016.

(51) Int. Cl.
    *B25J 15/02*     (2006.01)
    *A61B 34/30*     (2016.01)
    *F16C 11/12*     (2006.01)

(52) U.S. Cl.
    CPC .............. *A61B 2017/2927* (2013.01); *A61B 2017/2939* (2013.01); *A61B 2034/305* (2016.02); *F16C 11/12* (2013.01)

(58) Field of Classification Search
    CPC .. A61B 2017/00309; A61B 2017/2927; A61B 2017/2939; A61B 2017/00305; A61B 2017/003; A61B 2034/305
    See application file for complete search history.

(56) References Cited

U.S. PATENT DOCUMENTS

| | | |
|---|---|---|
| 4,165,745 A | 8/1979 | Heifetz |
| 4,540,211 A | 9/1985 | Masserang |
| 5,317,952 A | 6/1994 | Immega |
| 5,318,589 A | 6/1994 | Lichtman |
| 5,335,418 A | 8/1994 | Krivec |
| 5,496,317 A | 3/1996 | Goble et al. |
| 5,899,914 A | 5/1999 | Zirps et al. |
| 6,215,081 B1 | 4/2001 | Jensen et al. |
| 6,368,290 B1 | 4/2002 | Baska |
| 6,491,626 B1 | 12/2002 | Stone et al. |
| 6,676,684 B1 | 1/2004 | Morley et al. |
| 7,320,700 B2 | 1/2008 | Cooper et al. |
| 8,245,595 B2 | 8/2012 | Milenkovic |
| 8,308,801 B2 | 11/2012 | Halverson et al. |
| 8,323,297 B2 | 12/2012 | Hinman et al. |
| 8,567,033 B2 | 10/2013 | Macnamara |
| 8,597,280 B2 | 12/2013 | Cooper et al. |
| 8,708,593 B2 | 4/2014 | Stratton et al. |
| 8,911,471 B2 | 12/2014 | Spivey et al. |
| 8,945,174 B2 | 2/2015 | Blumenkranz et al. |
| 10,060,469 B2 | 8/2018 | Jimenez et al. |
| 10,285,763 B2 | 5/2019 | Vale et al. |
| 11,123,145 B2 | 9/2021 | Dearden et al. |
| 2005/0119527 A1 | 6/2005 | Banik et al. |
| 2005/0216033 A1 | 9/2005 | Lee et al. |
| 2006/0184198 A1 | 8/2006 | Bales et al. |
| 2006/0190034 A1 | 8/2006 | Nishizawa et al. |
| 2007/0208375 A1 | 9/2007 | Nishizawa et al. |
| 2008/0196533 A1 | 8/2008 | Bergamasco et al. |
| 2009/0198272 A1 | 8/2009 | Kerver et al. |
| 2009/0209960 A1 | 8/2009 | Chojin |
| 2010/0152574 A1* | 6/2010 | Erdman ............ A61M 25/0074 |
| | | 604/533 |
| 2010/0160735 A1 | 6/2010 | Bakos |
| 2010/0160940 A1 | 6/2010 | Lutze et al. |
| 2011/0276085 A1 | 11/2011 | Krzyzanowski et al. |
| 2011/0301599 A1 | 12/2011 | Roy et al. |
| 2013/0041392 A1 | 2/2013 | Edwards |
| 2013/0046317 A1 | 2/2013 | Blumenkranz |
| 2015/0157355 A1 | 6/2015 | Price et al. |
| 2016/0000423 A1 | 1/2016 | Shields et al. |
| 2016/0015428 A1 | 1/2016 | Bowden et al. |
| 2016/0022365 A1 | 1/2016 | Jensen et al. |
| 2016/0045096 A1 | 2/2016 | Kappel et al. |
| 2016/0051274 A1 | 2/2016 | Howell et al. |
| 2016/0287279 A1 | 10/2016 | Bovay et al. |
| 2017/0042562 A1 | 2/2017 | Moody et al. |
| 2018/0333164 A1 | 11/2018 | Arata et al. |
| 2019/0290375 A1 | 9/2019 | Dearden et al. |
| 2020/0008827 A1 | 1/2020 | Dearden et al. |
| 2020/0085415 A1 | 3/2020 | Dearden et al. |
| 2021/0369371 A1 | 12/2021 | Dearden et al. |

FOREIGN PATENT DOCUMENTS

| | | |
|---|---|---|
| CN | 102369332 A | 3/2012 |
| CN | 105055055 A | 11/2015 |
| DE | 19537320 A1 | 4/1997 |
| EP | 1151723 A2 | 11/2001 |
| WO | WO-2010078520 A2 | 7/2010 |
| WO | WO-2015057990 A1 | 4/2015 |
| WO | WO-2016123139 A2 | 8/2016 |
| WO | WO-2017189272 A1 | 11/2017 |
| WO | WO-2018052939 A1 | 3/2018 |

OTHER PUBLICATIONS

Office Action for European Application No. 17851420.4, mailed Nov. 3, 2022, 5 pages.

Choi D.Y., et al., "Flexure-Based Manipulator for Active Handheld Microsurgical Instrument," Proceedings of the IEEE 27th Annual Conference on Engineering in Medicine and Biology, Sep. 2005, pp. 5085-5088.

Doria M., et al., "Design of an Underactuated Compliant Gripper for Surgery Using Nitinol," Journal of Medical Devices, Mar. 2009, vol. 3 (1), Abstract, p. 011007, ASME.

Edmondson B.J., et al., "Oriceps: Origami-Inspired Forceps," ASME 2013 Conference on Smart Materials, Adaptive Structures and Intelligent Systems, Sep. 16-18, 2013, 6 pages.

Extended European Search Report for Application No. EP17851420.4 mailed on May 27, 2020, 8 pages.

Guerinot A.E., et al., "Compliant Joint Design Principles for High Compressive Load Situations," Journal of Mechanical Design, Department of Mechanical Engineering, Brigham Young University, Jul. 2005, vol. 127 (4), pp. 774-781.

Halverson P.A., "Multi-stable Compliant Rolling-contact Elements," Brigham Young University, May 3, 2007, 61 pages.

International Search Report and Written Opinion for Application No. PCT/US2017/051276, mailed on Dec. 26, 2017, 14 pages (BYUX00006/PCT).

Kota S. et al., "Design and Application of Compliant Mechanisms for Surgical Tools." Technical Briefs, Journal of Biomechanical Engineering, Nov. 2005, vol. 127, pp. 981-989, ASME.

Lassooij J., et al., "A Statically Balanced and Bi-stable Compliant End Effector Combined with a Laparoscopic 2DoF Robotic Arm," Journal of Mechanical Sciences, 2012, vol. 3, pp. 85-93.

Mertmann M., et al., "Grippers for the Micro Assembly Containing Shape Memory Actuators and Sensors," Le Journal de Physique IV France 7 (1997), Conference C5, Supplement of Journal de Physique III of Nov. 1997, pp. C5-621-C5-626.

Office Action for Chinese Application No. CN201780069597.7, mailed Feb. 8, 2022, 26 pages.

Office Action for Chinese Application No. CN201780069597.7, mailed Sep. 10, 2021, 13 pages.

Office Action for EP Application No. EP17851420.4, mailed Jan. 17, 2022, 6 pages.

Office Action for U.S. Appl. No. 16/332,515, mailed Dec. 7, 2021, 15 pages.

Office Action mailed Jul. 2, 2021 for EP Application No. 17851420.4 filed Sep. 13, 2017, 6 pages.

Office Action mailed Mar. 3, 2021 for Chinese Application No. 20178069597 filed Sep. 13, 2017, 17 pages.

Ramu G., et al., "A Flexure-based Deployable Stereo Vision Mechanism and Temperature and Force Sensors for Laparoscopic Tools," 14th National Conference on Machines and Mechanisms (NaCoMM09), Dec. 17-18, 2009, NaCoMM-2009-BMGR2, pp. 440-445.

Sahai R., et al., "Semi-Automated Micro Assembly for Rapid Prototyping of a One DOF Surgical Wrist," International Conference on Intelligent Robots and Systems (IROS 2003), Oct. 27-31, 2003, vol. 2, pp. 1882-1888, IEEE.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Zubir M.N.M., et al., "Development of a novel flexure based microgripper for precision manipulation of micro-objects," IEEE

(56) References Cited

OTHER PUBLICATIONS

International Conference on Industrial Technology (ICIT 2009), 2009, pp. 1-6.

* cited by examiner

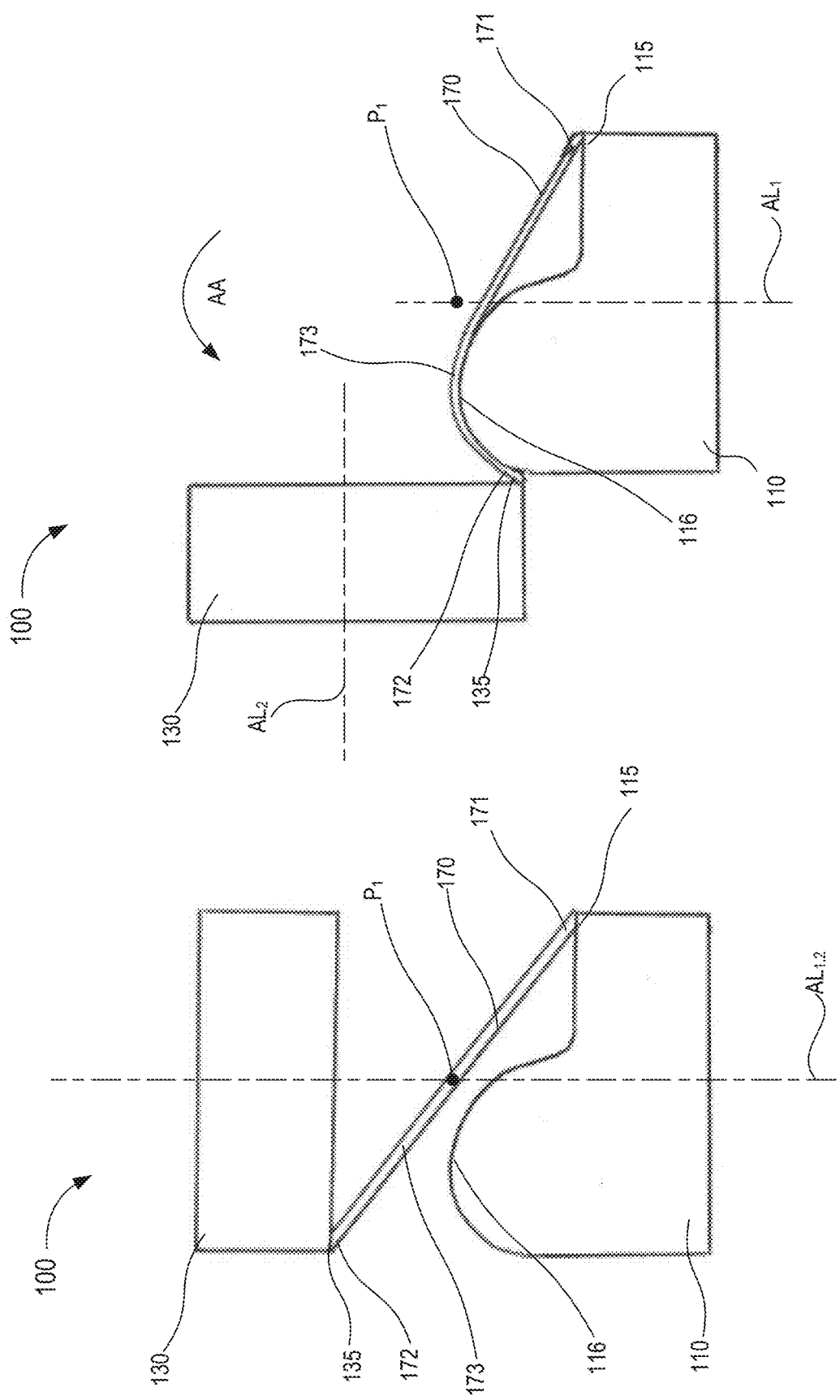

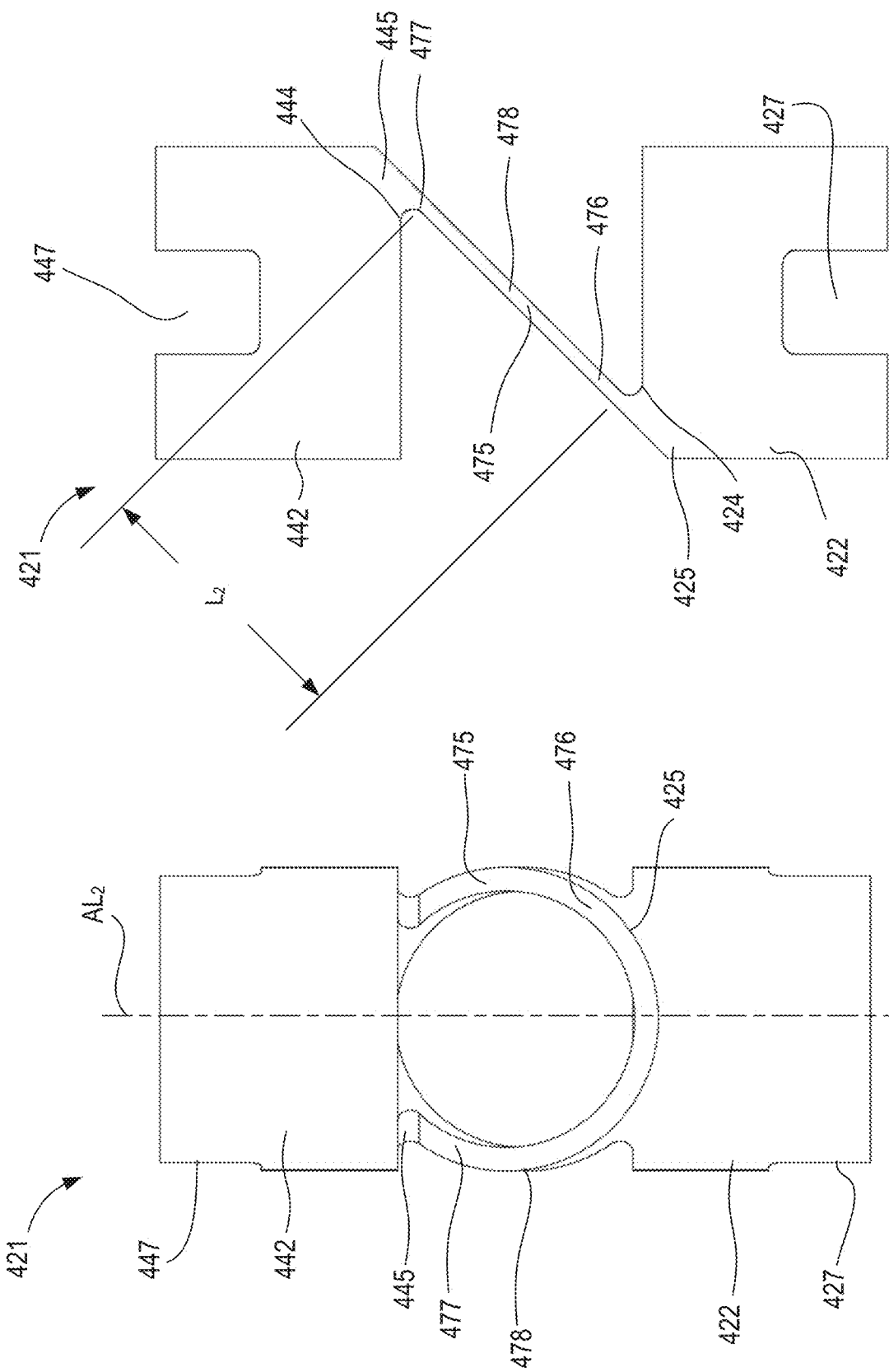

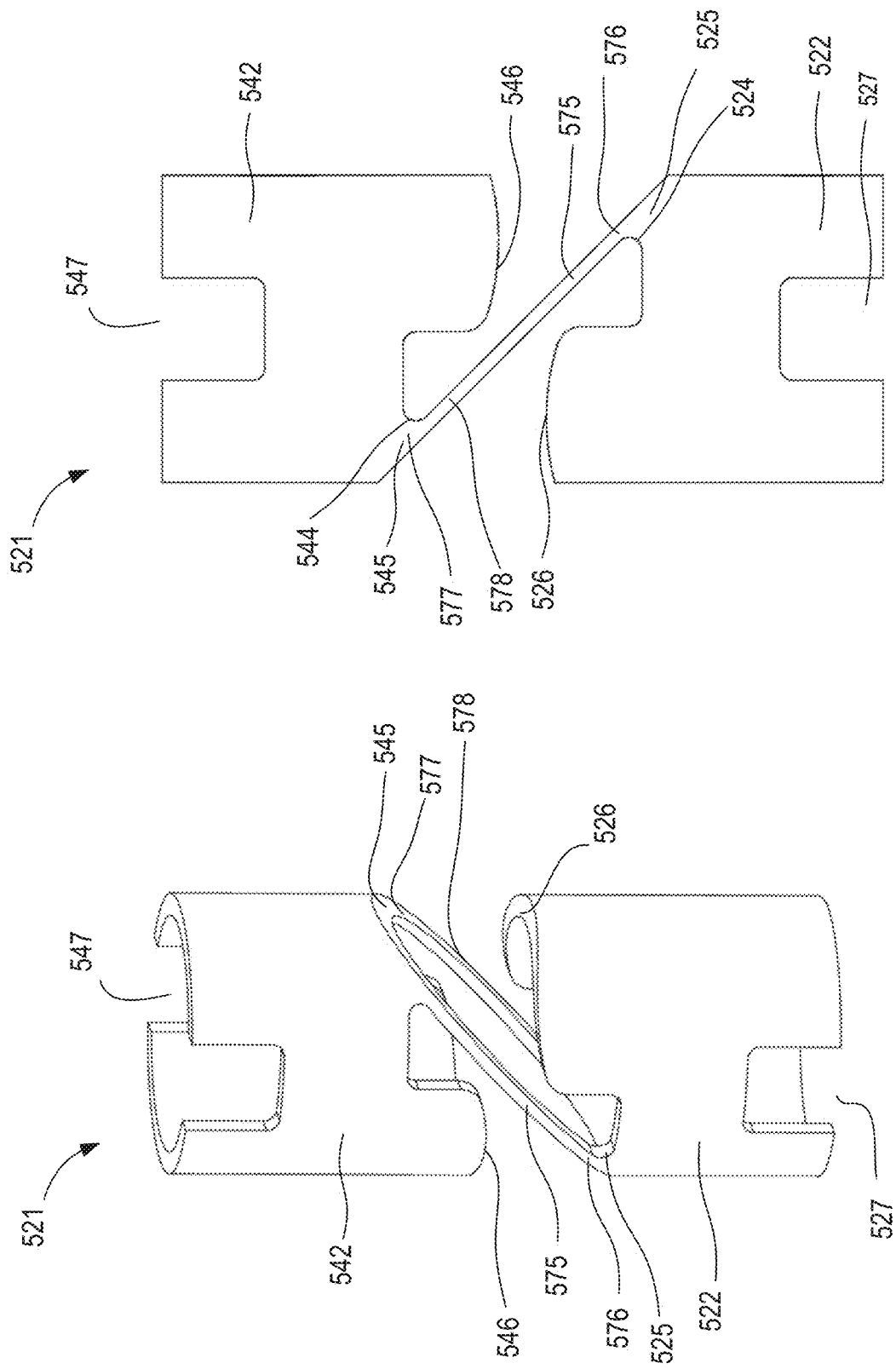

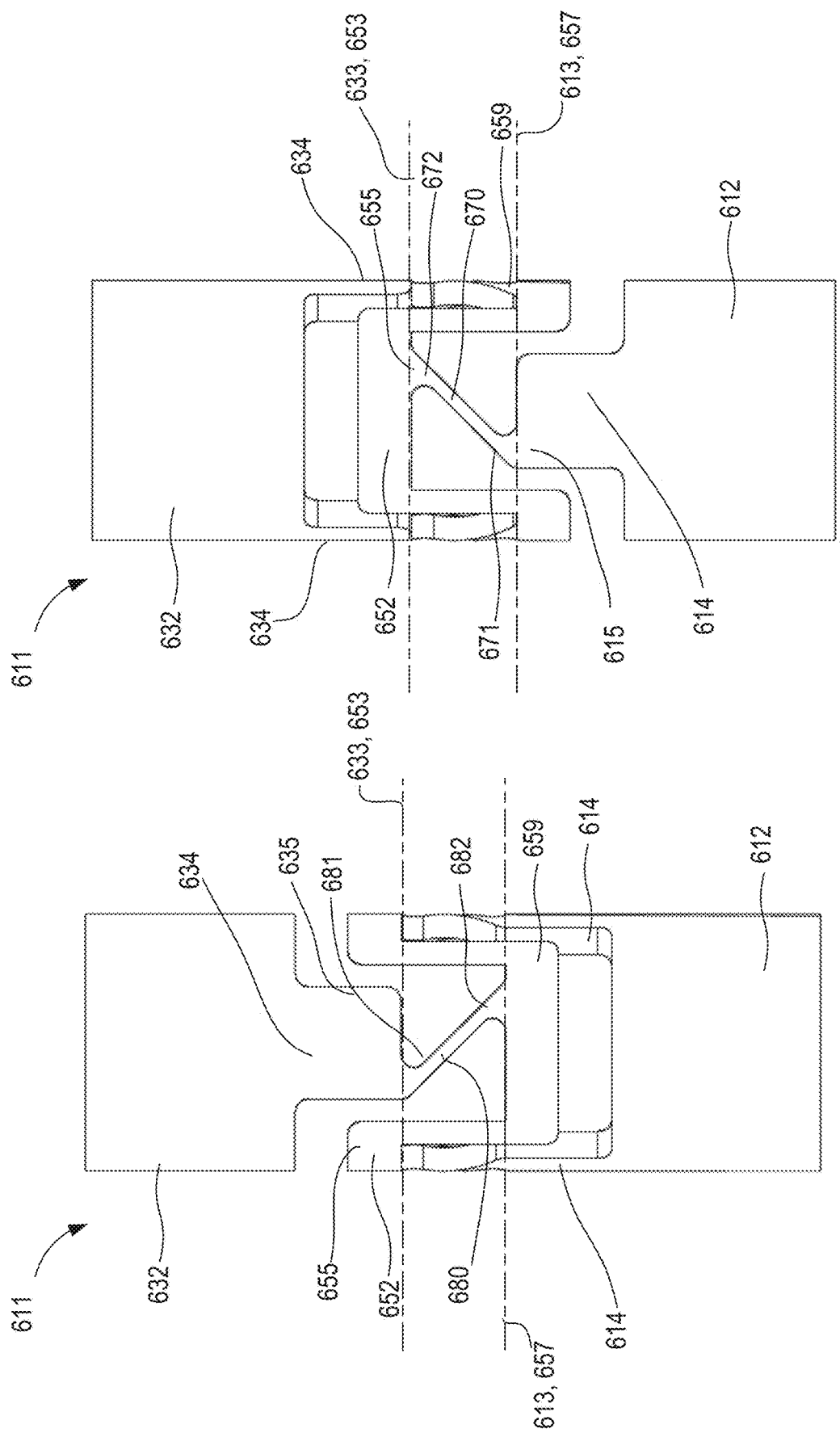

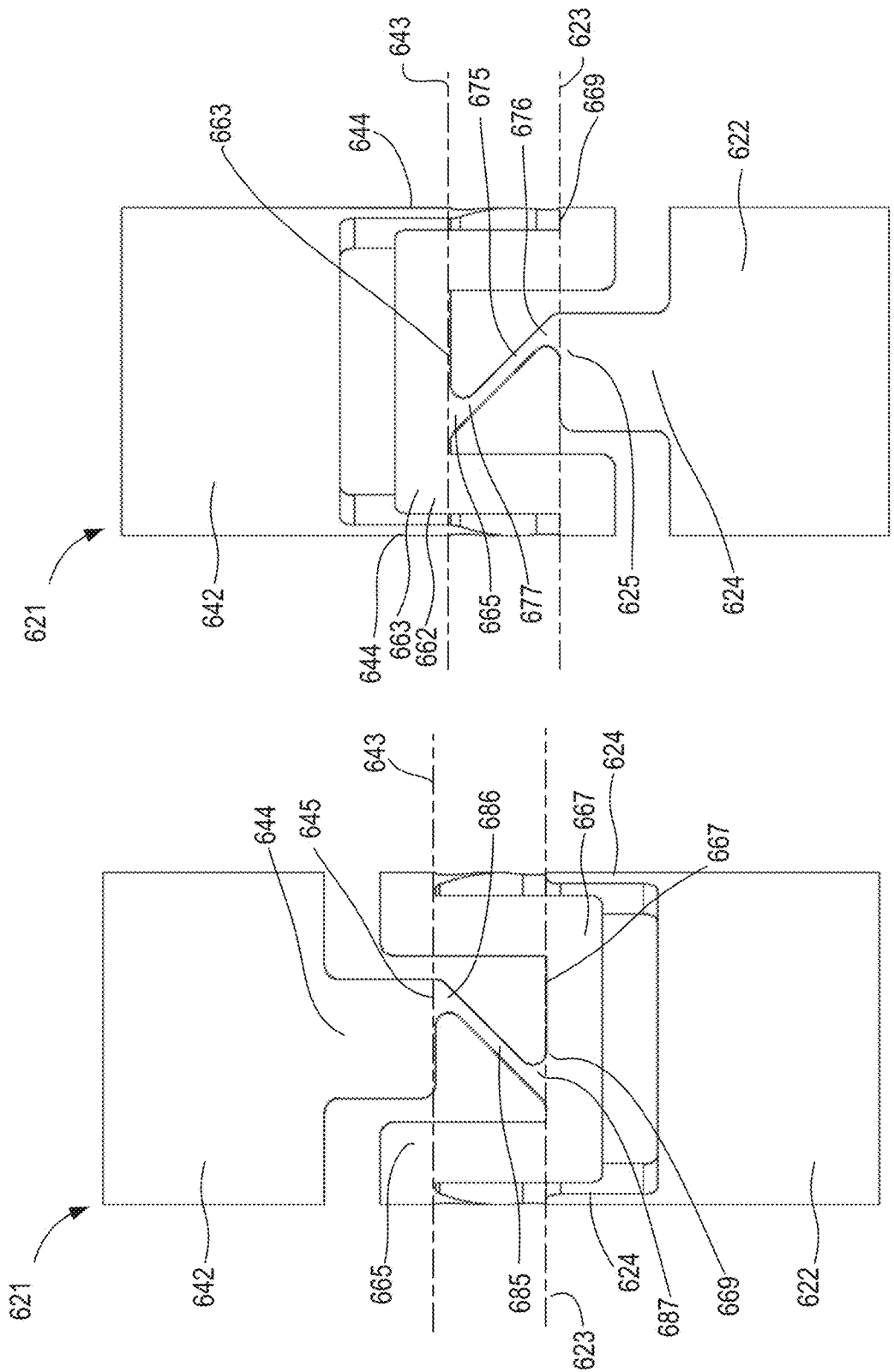

JOINT ASSEMBLIES WITH CROSS-AXIS FLEXURAL PIVOTS

CROSS-REFERENCE TO RELATED APPLICATIONS

This application is a continuation of U.S. application Ser. No. 16/332,515 (filed Mar. 12, 2019) (entitled "Joint Assemblies with Cross-Axis Flexural Pivots"), which is a U.S. national stage filing under 35 U.S.C. § 371 of International Application No. PCT/US2017/051276 (filed Sep. 13, 2017) (entitled "Joint Assemblies with Cross-Axis Flexural Pivots"), which claims benefit of priority to U.S. Provisional Application Ser. No. 62/394,310 (filed Sep. 14, 2016) (entitled "Joint Assemblies with Cross-Axis Flexural Pivots"), each of which is incorporated herein by reference in its entirety.

BACKGROUND

The embodiments described herein relate to compliant joint mechanisms. More particularly, the embodiments described herein relate to devices having a cross-axis flexural pivot that can be used, for example, in surgical applications.

Minimally Invasive Surgery (MIS) is a growing field, and known techniques employ tools to manipulate tissue that are both manually controlled or robotically controlled. Such known tools and mechanisms include, for example, kinematic chains including wrist mechanisms, steerable segments, grippers, cutting tools, or the like. Known methods include accessing a target work site inside a patient by at least partially following a natural lumen, such as the digestive tract, blood-carrying lumens, bronchi, or other lumens, of the patient. Following a natural lumen, for example, can allow a surgeon to operate at a work site while making fewer and/or smaller incisions through healthy tissue, although an incision may be needed at locations where the surgical device enters or leaves a natural lumen. In other MIS aspects, a surgical site is accessed without following a body lumen. Access may be via one or more incisions through the patient's body wall or via a natural orifice.

Surgeons and engineers are making continual efforts to mitigate the negative effects of surgery on patients. Reducing the size and/or the operating footprint of the surgical instruments is one method pursued in this effort. For example, when the instruments approach approximately 3 mm in diameter, they also approach a threshold where the entry incisions can be small enough so that little or no visible scar is left on the patient. But, some known tools having a diameter less than 3 mm lack the desired flexibility and may include mechanisms that produce an undesirably large swept volume inside the patient (e.g., operating footprint). For example, some known tools may lack wrist articulation and typically have one mechanical Degree of Freedom (DoF), such as grip performed by jaws. Other known tools have both wrist articulation and gripping function, but are characterized by a relatively large throw distance from the tool shaft axis to the end effector tip to accommodate the wrist articulation. Such tool designs, therefore, require more volume at a surgical site for effective tissue manipulation.

Some known instruments employ joint assemblies (e.g., for grippers or articulated shafts) that include a pin-in-slot joint to allow one portion of the tool (e.g., a first end of a shaft) to rotate relative to a second part of the tool (e.g., a second end of the shaft). Such known joint mechanisms are referred to as "non-compliant" revolute joints. Such known joints can be subject to undesirable levels of friction, wear, and undesirable motion, all of which leads to a decline in performance.

Other known instruments employ joint assemblies that include a flexible member that deforms in response to an input force to produce mobility within the joint. Such joint mechanisms are referred to as "compliant joints" or "compliant mechanisms." The use of compliant mechanisms can reduce the friction, wear, and the number of parts in the joint. Some known compliant mechanisms, however, lack stability and can be susceptible to fatigue or failure due to the deformation of the flexible member. Thus, some known compliant mechanisms are operable only over limited ranges of motion (e.g., angular ranges of motion). Additionally, the minimum size of some known compliant mechanisms can be limited as a result of the high stresses during deformation of the flexible member(s).

Thus, a need exists for improved joint mechanisms for surgical instruments and methods of assembly and use of such improved joint mechanisms.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, an apparatus includes a first joint member, a second joint member, and a flexure. The first joint member includes a connection portion and a contact surface. The second joint member including a connection portion. The flexure has a first end portion, a second end portion, and a central portion between the first end portion and the second end portion. The first end portion is coupled to the connection portion of the first joint member, and the second end portion is coupled to the connection portion of the second joint member. The flexure is configured to deform elastically when the first joint member and the second joint member move from a first configuration to a second configuration. The central portion of the flexure is spaced apart from the contact portion when the first joint member and the second joint member are in the first configuration. The central portion of the flexure contacts the contact portion when the first joint member and the second joint member are in the second configuration.

In some embodiments, an apparatus includes a cross-axis flexural pivot arrangement that allows for two or more degrees of freedom. The apparatus includes a first joint member, a second joint member, a third joint member between the first joint member and the second joint member, a first flexure, and a second flexure. The first flexure has a first end portion coupled to the first joint member, and a second end portion coupled to the third joint member. The first flexure is configured to deform elastically when the second joint member rotates relative to the first joint member about a first axis of rotation. The second flexure has a first end portion coupled to the second joint member, and a second end portion coupled to the third joint member. The second flexure is configured to deform elastically when the second joint member rotates relative to the first joint member about a second axis of rotation. The second axis of rotation nonparallel to and intersecting with the first axis of rotation.

BRIEF DESCRIPTION OF THE DRAWINGS

FIGS. 1 and 2 are schematic illustrations of a compliant joint mechanism according to an embodiment, in a first configuration and a second configuration, respectively.

FIGS. 11 and 12 are a side view and a front view, respectively, of the inner member of the compliant joint mechanism shown in FIG. 10.

FIGS. 15 and 16 are a perspective view and a front view, respectively, of an outer member of the compliant joint mechanism shown in FIGS. 13 and 14.

FIGS. 27 and 28 are a side view and a front view, respectively, of the inner member of the compliant joint mechanism shown in FIGS. 25 and 26.

FIGS. 31 and 32 are a side view and a front view, respectively, of the outer member of the compliant joint mechanism shown in FIGS. 23 and 24.

DETAILED DESCRIPTION

Figure 3:
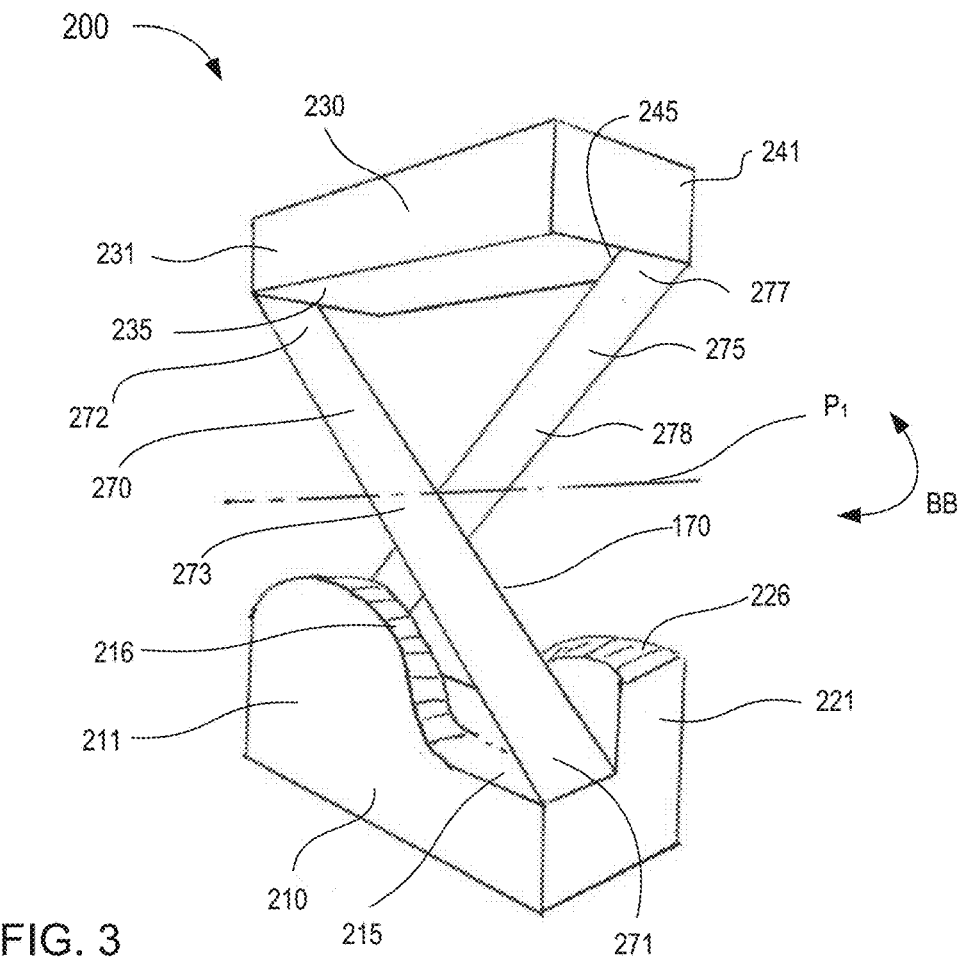
FIG. 3 is a schematic illustration of a compliant joint mechanism having two cross-axis flexures, according to an embodiment.

The embodiments described herein can advantageously be used in a wide variety of grasping, cutting, and manipulating operations. In particular, the cross-axis flexure designs described herein can allow a single compliant joint to deflect to produce both gripping motion and wrist motion of an end effector tool with respect to a mounting shaft. As described herein, the cross-axis flexure designs can include a contact (or "cam") surface so that the loads on the flexure are controlled, thus limiting stress. In this manner, the range of motion can be increased (up to 85 degrees of rotation or more) and the nominal size of the joint assembly can be decreased. The embodiments described herein also include joints with two degrees of freedom that minimize or reduces friction. The embodiments described herein have mechanisms providing relatively low friction. The embodiments described herein include at least a two-degree-of-freedom tool at small scales, and that has a minimum or reduced number of parts. In other embodiments, however, a tool, a joint assembly, or both, has only one degree-of-freedom.

In some embodiments, an apparatus includes an apparatus includes a first joint member, a second joint member, and a flexure. The first joint member includes a connection portion and a contact surface. The second joint member including a connection portion. The flexure has a first end portion, a second end portion, and a central portion between the first end portion and the second end portion. The first end portion is coupled to the connection portion of the first joint member, and the second end portion is coupled to the connection portion of the second joint member. The flexure is configured to deform elastically when the first joint member and the second joint member move from a first configuration to a second configuration. The central portion of the flexure is spaced apart from the contact portion when the first joint member and the second joint member are in the first configuration. The central portion of the flexure contacts the contact portion when the first joint member and the second joint member are in the second configuration.

In some embodiments, an apparatus includes a cross-axis flexural pivot arrangement that allows for two or more degrees of freedom. The apparatus includes a first joint member, a second joint member, a third joint member between the first joint member and the second joint member, a first flexure, and a second flexure. The first flexure has a first end portion coupled to the first joint member, and a second end portion coupled to the third joint member. The first flexure is configured to deform elastically when the second joint member rotates relative to the first joint member about a first axis of rotation. The second flexure has a first end portion coupled to the second joint member, and a second end portion coupled to the third joint member. The second flexure is configured to deform elastically when the second joint member rotates relative to the first joint member about a second axis of rotation. The second axis of rotation nonparallel to and intersecting with the first axis of rotation Methods of fabricating a joint assembly are also described herein. In some embodiments, a method includes producing a joint member in a material sheet when the material sheet is in a planar configuration. The joint member including a first end portion, a second end portion, and a flexure between the first end portion and the second end portion. After the producing, the material sheet is rolled such that the first end portion forms a first cylinder about a longitudinal axis and the second end portion forms a second cylinder about the longitudinal axis. The method further includes joining a first side of the material sheet to a second side of the material sheet.

As used herein, the term "about" when used in connection with a referenced numeric indication means the referenced numeric indication plus or minus up to 10% of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g. a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein. A flexible part may have infinite degrees of freedom (DOF's).

Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links.

As used in this specification and the appended claims, the words "proximal" and "distal" refer to direction closer to and away from, respectively, an operator (or controller) of the surgical device. Thus, for example, the end of a joint assembly that is farthest away from the user (and that is closest to the target tissue) would be the distal end of the joint assembly, while the end opposite the distal end (i.e., the end manipulated by the user or coupled to the actuation shaft) would be the proximal end of the joint assembly.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, joint mechanism, joint assembly, and variants thereof, can be interchangeably used.

Aspects of the invention are described primarily in terms of an implementation using a surgical system, such as, for example, the da Vinci® Surgical System, commercialized by Intuitive Surgical, Inc. of Sunnyvale, California Examples of such surgical systems are the da Vinci® Xi™ Surgical System (Model IS4000) and the da Vinci® Si™ HD™ Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200), or any other surgical assemblies, are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIGS. 1 and 2 are schematic illustrations of a compliant joint assembly 100, according to an embodiment. The joint assembly 100 includes a first joint member 110, a second joint member 130, and a flexure 170. The joint assembly 100, and any of the joint assemblies described herein, can be used in any suitable surgical device or system as described herein. For example, the joint assembly 100 or any of the components therein are optionally parts of an end effector (such as a gripper, shears, or the like), an articulating shaft, a wrist assembly, or the like. Either of the first joint member 110 or the second joint member 130 can be coupled to an end of a surgical instrument shaft to form a wrist assembly that allows the end effector to change orientation (e.g., one or more of roll, pitch, and yaw) with reference to the shaft.

The first joint member 110 includes a connection portion 115 and a contact surface 116, and defines a first axis $AL_1$. The first joint member 110 can be any suitable shape. For example, in some embodiments, the first joint member 110 can be an elongated member, and the first axis $AL_1$ can be a longitudinal center line of the first joint member 110. In other embodiments, the first joint member 110 can include a planar surface that opposes a corresponding planar surface of the second joint member 130, and the first axis $AL_1$ can be an axis normal to the opposing planar surfaces. The connection portion 115 can be at any suitable location on the first joint member 110, and can have any suitable properties to couple the first joint member 110 to the flexure 170, as described herein. For example, in some embodiments, the connection portion 115 can be a surface (i.e., a connection surface) to which the flexure 170 is coupled. In other embodiments, the connection portion 115 can include a protrusion, a recess, a fastener, or any other suitable fastening mechanism. In yet other embodiments, the connection portion 115 can be monolithically formed (i.e., can be integrally formed with) the flexure 170.

The contact surface 116 can be any suitable surface that contacts the flexure 170 during use, as described below. Although shown as being a curved surface, in other embodiments, the contact surface 116 can be a planar surface. In other embodiments, the contact surface 116 can have a specific profile or shape. For example, in some embodiments, the contact surface 116 can define a radius of curvature selected to control the bending of the flexure 170 during use.

The second joint member 130 includes a connection portion 135, and defines a second axis $AL_2$. The second joint member 130 can be any suitable shape. For example, in some embodiments, the second joint member 130 can be an elongated member, and the second axis $AL_2$ can be a longitudinal center line of the second joint member 130. In other embodiments, the second joint member 130 can include a planar surface that opposes a corresponding planar surface of the first joint member 110, and the second axis $AL_2$ can be an axis normal to the opposing planar surfaces. The connection portion 135 can be at any suitable location on the second joint member 130, and can have any suitable properties to couple the second joint member 130 to the flexure 170, as described herein. For example, in some embodiments, the connection portion 135 can be a surface (i.e., a connection surface) to which the flexure 170 is coupled. In other embodiments, the connection portion 135 can include a protrusion, a recess, a fastener, or any other suitable fastening mechanism. In yet other embodiments, the connection portion 135 can be monolithically formed (i.e., can be integrally formed with) the flexure 170.

The first joint member 110 is coupled to the second joint member 130 via the flexure 170. More specifically, the flexure 170 has a first end portion 171, a second end portion 172, and a central portion 173 between the first end portion 171 and the second end portion 172. The first end portion 171 is coupled to the connection portion 115 of the first joint member 110, and the second end portion 172 is coupled to the connection portion 135 of the second joint member 130. As shown in FIG. 2, the flexure 170 deforms elastically when the second joint member 130 moves relative to the first joint member 110. Similarly stated, the flexure deforms elastically when the first joint member 110 and the second joint member 130 move from a first configuration (FIG. 1) to a second configuration (FIG. 2). Thus, the flexure 170 is a resilient member that stores energy from an actuation force and releases the energy when the actuation force is removed, thus allowing the joint assembly 100 to repeatedly be moved between the first configuration (FIG. 1) to the second configuration (FIG. 2), or any other suitable configurations. This arrangement results in a joint assembly with low part count, reduced friction, and the ability to scale the device to smaller sizes, as compared to a traditional pin joint.

As shown, when the joint assembly 100 is in the first configuration (FIG. 1), the central portion 173 of the flexure 170 is spaced apart from the contact surface 116. When the joint assembly 100 is in the second configuration (FIG. 2), the central portion 173 of the flexure 170 contacts the contact surface 116. In this manner, the contact surface 116 can control the deformation of the flexure 170. Similarly stated, the engagement between the contact surface 116 and the central portion 173 of the flexure 170 when the first joint member 110 and the second joint member 130 move from the first configuration to the second configuration constrains the radius of curvature of the flexure 170. This can, in turn, limit the stress in the flexure 170 and maintain a substantially constant stress during the deformation of the flexure 170.

As shown in FIG. 2, when the joint assembly 100 transitions from the first configuration to the second configuration, the second joint member 130 rotates relative to the first joint member 110, as shown by the arrow AA. Thus, in some embodiments, the second axis $AL_2$ is coaxial with the first axis $AL_1$ when the joint assembly 100 is in the first configuration, and the second axis $AL_2$ is non-coaxial with the first axis $AL_1$ when the joint assembly 100 is in the second configuration. Moreover, the second joint member 130 rotates relative to the first joint member 110 about an axis of rotation (also referred to as a pivot axis), indicated by $P_1$ in FIGS. 1 and 2. In some embodiments, the axis of rotation $P_1$ can be approximated as the center point along the flexure 170 when the joint assembly 100 is in the first configuration. For example, as shown, in such embodiments, the first axis $AL_1$ can intersect the axis of rotation $P_1$. Moreover, either of the first axis $AL_1$ or the second axis $AL_2$ can be normal to the axis of rotation $P_1$. In other embodiments, however, the axis of rotation $P_1$ can non-intersecting with either of the first axis $AL_1$ or the second axis $AL_2$, or can be at any angle relative to either of the first axis $AL_1$ or the second axis $AL_2$.

In some embodiments, the axis of rotation $P_1$ can be approximated as being at a substantially constant location relative to the first joint member 110 during movement of the second joint member 130. For example, in some embodiments, a joint assembly can include multiple flexures or constraints to maintain a substantially constant axis of rotation $P_1$. In other embodiments, a joint assembly can be configured such that the axis of rotation $P_1$ translates when the joint assembly transitions from the first configuration to the second configuration. In yet other embodiments, the second joint member can translate relative to the first joint member when the joint assembly transitions from the first configuration to the second configuration. For example, in some embodiments, the second joint member can both rotate and translate relative to the first joint member when the joint assembly transitions from the first configuration to the second configuration.

The first joint member 110 can include any suitable spatial relationship between the axis of rotation $P_1$, the first axis $AL_1$, the contact surface 116, and the connection portion 115. For example, as shown, in some embodiments, the first axis $AL_1$ can intersect the axis of rotation $P_1$, and can be between the contact surface 116 and the connection portion 115. Similarly stated, the contact surface 116 can be on one side of the first axis $AL_1$ and the connection portion 115 (and therefore, the first end portion 171 of the flexure) can be on the other side of the first axis $AL_1$. Further, in some embodiments, the contact surface 116 can be between the axis of rotation $P_1$ and the connection portion 115. Similarly stated, the contact surface 116 can extend from (or protrude from) the connection portion 115 in a direction along the first axis $AL_1$ towards the axis of rotation $P_1$. Such arrangements can, for example, provide the desired kinematic performance of the joint assembly 100 or any of the joint assemblies shown and described herein.

Although not shown in FIGS. 1 and 2, the force to move the second joint member 130 relative to the first joint member 110 (referred to as the actuation force) can be applied to any suitable portion of the joint assembly 100 by any suitable mechanism. For example, in some embodiments, the second joint member 130 can include an engagement portion that receives the actuation force to transition the joint assembly 100 from the first configuration to the second configuration. In some embodiments, the actuation force can be applied via a flexible cable or a rigid rod at a fixed point on the second joint member 130. In other embodiments, the actuation force can be applied via a flexible cable or a rigid rod at multiple points on the second joint member 130.

Although shown as including a single flexure 170, in other embodiments, a joint assembly can include any suitable number and arrangement of flexures. For example, in some embodiments, a joint assembly can include two (or more) flexures that are non-parallel to each other. Similarly stated, in some embodiments, a joint assembly can include two flexures, the center axes of which cross each other. This is referred to as a cross-axis flexure joint. FIG. 3 is a schematic illustration of a compliant joint assembly 200, according to an embodiment. The joint assembly 200 includes a first joint member 210, a second joint member 230, a first flexure 270, and a second flexure 275. The joint assembly 200, and any of the joint assemblies described herein, can be used in any suitable surgical device or system as described herein. For example, the joint assembly 200 or any of the components therein are optionally parts of an end effector (such as a gripper, shears, or the like), an articulating shaft, a wrist assembly, or the like. Either of the first joint member 210 or the second joint member 230 can be coupled to an end of a surgical instrument shaft to form a wrist assembly that allows the end effector to change orientation (e.g., one or more of roll, pitch, and yaw) with reference to the shaft.

The first joint member 210 includes an inner portion 211 and an outer portion 221. The inner portion 211 includes a connection portion 215 and a contact surface 216. The connection portion 215 can be at any suitable location on the inner portion 211 of the first joint member 210, and can have any suitable properties to couple the first joint member 210 to the first flexure 270, as described herein. For example, in some embodiments, the connection portion 215 can be a surface (i.e., a connection surface) to which the first flexure 270 is coupled (e.g., via welding, adhesive, or the like). In other embodiments, the connection portion 215 can include a protrusion, a recess, a fastener, or any other suitable fastening mechanism. In yet other embodiments, the connection portion 215 can be monolithically formed (i.e., can be integrally formed with) the first flexure 270.

The contact surface 216 can be any suitable surface that contacts the first flexure 270 during use, as described below. Although shown as being a curved surface, in other embodiments, the contact surface 216 can be a planar surface. In other embodiments, the contact surface 216 can have a specific profile or shape. For example, in some embodiments, the contact surface 216 can define a radius of curvature selected to control the bending of the first flexure 270 during use.

The outer portion 221 of the first joint member 210 includes a connection portion (not shown) and a contact surface 226. The connection portion can be similar to the connection portion 215, and can be at any suitable location on the outer portion 221 of the first joint member 210, and can have any suitable properties to couple the first joint member 210 to the second flexure 275, as described herein. For example, in some embodiments, the connection portion 225 can be a surface (i.e., a connection surface) to which the second flexure 275 is coupled (e.g., via welding, adhesive, or the like). In other embodiments, the connection portion 225 can include a protrusion, a recess, a fastener, or any other suitable fastening mechanism. In yet other embodiments, the connection portion 225 can be monolithically formed (i.e., can be integrally formed with) the second flexure 275.

The contact surface 226 can be any suitable surface that contacts the second flexure 275 during use, as described below. Although shown as being a curved surface, in other embodiments, the contact surface 226 can be a planar surface. In other embodiments, the contact surface 226 can have a specific profile or shape. For example, in some embodiments, the contact surface 226 can define a radius of curvature selected to control the bending of the second flexure 275 during use.

The second joint member 230 includes an inner portion 231 and an outer portion 241. The inner portion 231 corresponds to (or opposes) the inner portion 211, and the outer portion 241 corresponds to (or opposes) the outer portion 221. The inner portion 231 includes a connection portion 235 that has any suitable properties to couple the first joint member 210 to the first flexure 270. For example, in some embodiments, the connection portion 235 can be a surface (i.e., a connection surface) to which the first flexure 270 is coupled (e.g., via welding, adhesive, or the like). In other embodiments, the connection portion 215 can include a protrusion, a recess, a fastener, or any other suitable fastening mechanism. In yet other embodiments, the connection portion 235 can be monolithically formed (i.e., can be integrally formed with) the first flexure 270.

The outer portion 241 of the second joint member 230 includes a connection portion 245. The connection portion 245 can be similar to the connection portion 235, and can be at any suitable location on the outer portion 241 of the second joint member 230. The connection portion 245 can have any suitable properties to couple the second joint member 230 to the second flexure 275. For example, in some embodiments, the connection portion 245 can be a surface (i.e., a connection surface) to which the second flexure 275 is coupled (e.g., via welding, adhesive, or the like). In other embodiments, the connection portion 245 can include a protrusion, a recess, a fastener, or any other suitable fastening mechanism. In yet other embodiments, the connection portion 245 can be monolithically formed (i.e., can be integrally formed with) the second flexure 275.

The first joint member 210 is coupled to the second joint member 230 via the first flexure 270 and the second flexure 275. The first flexure 270 has a first end portion 271, a second end portion 272, and a central portion 273 between the first end portion 271 and the second end portion 272. The first end portion 271 is coupled to the connection portion 215 of the first joint member 210, and the second end portion 272 is coupled to the connection portion 235 of the second joint member 230. The second flexure 275 has a first end portion 276, a second end portion 277, and a central portion 278 between the first end portion 276 and the second end portion 277. The first end portion 276 is coupled to the connection portion (not shown) of the first joint member 210, and the second end portion 277 is coupled to the connection portion 245 of the second joint member 230.

In use, the first flexure 270 and the second flexure 275 each deform elastically when the second joint member 230 moves relative to the first joint member 210. Similarly stated, the first flexure 270 and the second flexure 275 deform elastically when the first joint member 210 and the second joint member 230 move from a first configuration (FIG. 3) to a second configuration (not shown). Thus, the flexures are resilient members that store energy from an actuation force and releases the energy when the actuation force is removed, thus allowing the joint assembly 200 to repeatedly be moved between the various configurations.

When the joint assembly 200 transitions from the first configuration to the second configuration, the second joint member 230 rotates relative to the first joint member 210, as shown by the arrow BB in FIG. 3. In particular, the second joint member 230 rotates relative to the first joint member 210 about an axis of rotation (also referred to as a pivot axis), indicated by $P_1$. In some embodiments, the axis of rotation $P_1$ can be approximated as the axis at which the first flexure 270 crosses the second flexure 275 when the joint assembly 200 is in the first configuration. For example, as shown, in such embodiments, the first axis $AL_1$ can intersect the axis of rotation $P_1$. In some embodiments, the axis of rotation $P_1$ can be approximated as being at a substantially constant location relative to the first joint member 210 during movement of the second joint member 230. In other embodiments, however, a joint assembly can be configured such that the axis of rotation $P_1$ is spaced apart from an axis at which the flexures cross, or the axis of rotation $P_1$ translates when the joint assembly transitions from the first configuration to the second configuration.

When the joint assembly 200 is in the first configuration (FIG. 3), the central portion 273 of the first flexure 270 is spaced apart from the contact surface 216. When the joint assembly 200 is in a second configuration (not shown), the second joint member 230 rotates counter-clockwise relative to the first joint member 210, and the central portion 273 of the first flexure 270 contacts the contact surface 216. In this manner, the contact surface 216 can control the deformation of the first flexure 270. Similarly stated, the engagement between the contact surface 216 and the central portion 273 of the first flexure 270 when the first joint member 210 and the second joint member 230 move from the first configuration to the second configuration constrains the radius of curvature of the first flexure 270. This can, in turn, limit the stress in the first flexure 270 and maintain a substantially constant stress during the deformation of the first flexure 270.

When the joint assembly 200 is in the first configuration (FIG. 3), the central portion 278 of the second flexure 275 is spaced apart from the contact surface 226. When the joint assembly 200 is in a third configuration (not shown), the second joint member 230 rotates clockwise relative to the first joint member 210, and the central portion 278 of the second flexure 275 contacts the contact surface 226. In this manner, the contact surface 226 can control the deformation of the second flexure 275. Similarly stated, the engagement between the contact surface 226 and the central portion 278 of the second flexure 275 when the first joint member 210 and the second joint member 230 move from the first configuration to the second configuration constrains the radius of curvature of the second flexure 275. This can, in turn, limit the stress in the second flexure 275 and maintain a substantially constant stress during the deformation of the second flexure 275.

Figure 4:
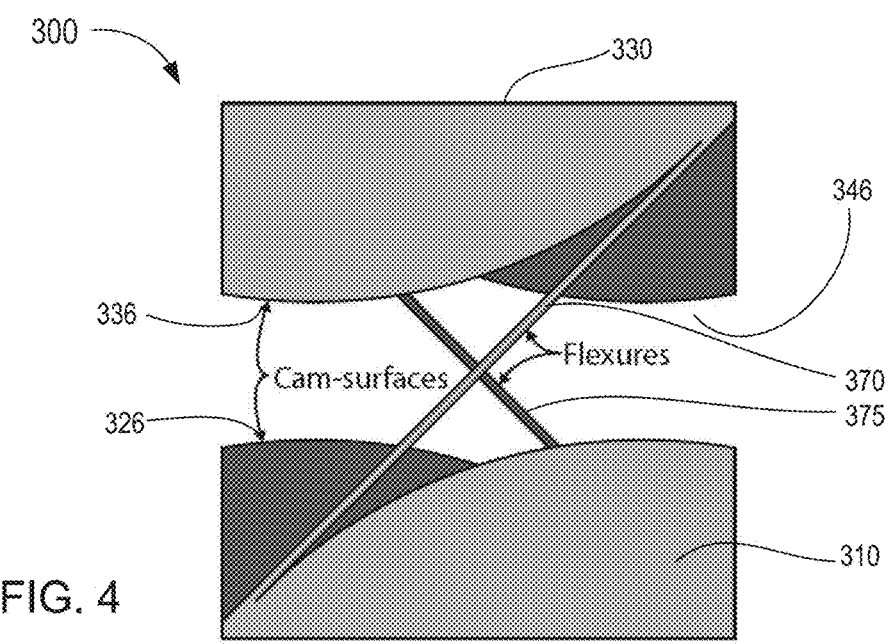
FIG. 4 is a schematic illustration of a compliant joint mechanism having two cross-axis flexures, according to an embodiment.

Although the joint assembly 200 is shown as including a first joint member 210 including contact surfaces 216, 226 and a second joint member 230 devoid of any contact surfaces, in other embodiments, a joint assembly can include any number of joint members (two, three, or more), each having any number of contact surfaces as described herein. For example, FIG. 4 is a schematic illustration of a joint member 300, according to an embodiment. The joint assembly 300 includes a first joint member 310, a second joint member 330, a first flexure 370, and a second flexure 375. The joint assembly 300, and any of the joint assemblies described herein, can be used in any suitable surgical device or system as described herein. For example, the joint assembly 300 or any of the components therein are optionally parts of an end effector (such as a gripper, shears, or the like), an articulating shaft, a wrist assembly, or the like. Either of the first joint member 310 or the second joint member 330 can be coupled to an end of a surgical instrument shaft to form a wrist assembly that allows the end effector to change orientation (e.g., one or more of roll, pitch, and yaw) with reference to the shaft. The joint assembly 300 can be similar in functionality to the joint member 200, the joint member 400 or any of the other joint members shown and described herein, and thus certain portions of the joint member 300 are not described in detail below.

The first joint member 310 includes a contact surface 316 and a contact surface 326. The contact surfaces 316, 326 can be any suitable surfaced that contact the first flexure 370 and the second flexure 375, respectively, during use. The second joint member 330 includes a contact surface 336 and a contact surface 346. The contact surfaces 336, 346 can be any suitable surfaced that contact the first flexure 370 and the second flexure 375, respectively, during use.

The first joint member 310 is coupled to the second joint member 330 via the first flexure 370 and the second flexure 375. In use, the first flexure 370 and the second flexure 375 each deform elastically when the second joint member 330 moves relative to the first joint member 310. Similarly stated, the first flexure 370 and the second flexure 375 deform elastically when the first joint member 310 and the second joint member 330 move from a first configuration (FIG. 4) to a second configuration and a third configuration (not shown). Thus, the flexures are resilient members that store energy from an actuation force and releases the energy when the actuation force is removed, thus allowing the joint assembly 300 to repeatedly be moved between the various configurations.

When the joint assembly 300 is in the first configuration (FIG. 4), the central portion of the first flexure 370 is spaced apart from the contact surface 316 and the contact surface 336. When the joint assembly 300 is in the first configuration, the central portion of the second flexure 375 is spaced apart from the contact surface 326 and the contact surface 346. When the joint assembly 300 is in a second configuration (not shown), the second joint member 330 rotates counter-clockwise relative to the first joint member 310. During this rotation, the central portion of the first flexure 370 contacts the contact surface 336, and the central portion of the second flexure 375 contacts the contact surface 326. When the joint assembly 300 moves to a third configuration (not shown), the second joint member 330 rotates clockwise relative to the first joint member 310. During this rotation, the central portion of the first flexure 370 contacts the contact surface 316 and the second flexure 375 contacts the contact surface 346. In this manner, the contact surfaces can control the deformation of the first flexure 370 and the second flexure 375. Similarly stated, the engagement between the contact surfaces and the first flexure 370 and the second flexure 375 constrains the radius of curvature of the first flexure 380 and the second flexure 375. This can, in turn, limit the stress in the flexures and maintain a substantially constant stress during the deformation of the flexures.

Controlling the curvature of a flexure (including any of the flexures described herein) can enable a larger deflection before the flexure yields. Although any of the flexures described herein can have any suitable shape, they can be modeled as thin, elastic beams. For thin, elastic beams bending moment (and therefore stress) is proportional to curvature and inversely proportional to the radius of curvature. The derivation of flexure stress with respect to the radius of curvature follows.

The applied moment, M, is related to the controlled radius of curvature, R', as given by Eq. (1) below, where E is the modulus of elasticity and I is the second moment of area. The maximum stress, $\sigma_{max}$, is given by Eq. (2), where h is the flexure thickness.

$$M = \frac{EI}{R'} \qquad \text{Eq. (1)}$$

$$\sigma_{max} = \frac{Mh}{2I} \qquad \text{Eq. (2)}$$

Substituting Eq. (1) into Eq. (2) results in the maximum bending stress as a function of the controlled radius of curvature:

$$\sigma_{max} \frac{Eh}{2R'} \qquad \text{Eq. (3)}$$

Constraining the radius of curvature of the flexure to be constant results in a constant stress along the member at a given distance from the neutral axis. To control the radius of curvature the contact surface (including any of the contact surfaces described herein) can be integrated into the joint assembly, such as for example, the joint assembly 300. The ratio of rotation of a joint assembly with contact surfaces (also referred to as cam surfaces) to rotation of a standard joint assembly without contact surfaces can be calculated as:

$$\frac{\theta_{cam}}{\theta} = \frac{\left(\frac{2S_y L}{Eh}\right)}{\left(\frac{2S_y L \cos\beta}{S_y Eh}\right)} = \frac{S_\theta}{\cos\beta} \qquad \text{Eq. (4)}$$

Where Sy is the yield strength of the material, L is the flexure length, β is the flexure angle, and $S_\theta$ is the stress coefficient (as defined by Jensen, B. D. and Howell, L. L., "The Modeling of Cross-Axis Flexural Pivots," Mechanism and Machine Theory 37 (5) (2002), pg 461-476). When the flexure angle is 45 degrees $\theta_{cam}/\theta=1.36$, meaning that a joint assembly mechanism with a contact (or cam) surface to guide the flexures will theoretically have a 36% increase in angular deflection until yield compared a standard joint assembly of similar geometry. This increased performance may be useful in a variety of applications.

Although the joint assembly 200 is shown and described as having planar joint members (e.g., the first joint member 210 and the second joint member 230), in other embodiments, a joint assembly can include joint members having any suitable shape. For example, in some embodiments, a joint assembly can include cylindrical joint members. FIGS. 5-12 are various views of a joint assembly 400 according to an embodiment. The joint assembly 400 includes a first joint member 410 and a second joint member 430 that are movably coupled together by a first flexure 470 and a second flexure 475. The joint assembly 400, and any of the joint assemblies described herein, can be used in any suitable surgical device or system as described herein. For example, the joint assembly 400 or any of the components therein are optionally parts of an end effector (such as a gripper, shears, or the like), an articulating shaft, a wrist assembly, or the like. Either of the first joint member 410 or the second joint member 430 can be coupled to an end of a surgical instrument shaft to form a wrist assembly that allows the end effector to change orientation (e.g., one or more of roll, pitch, and yaw) with reference to the shaft.

Figure 5:
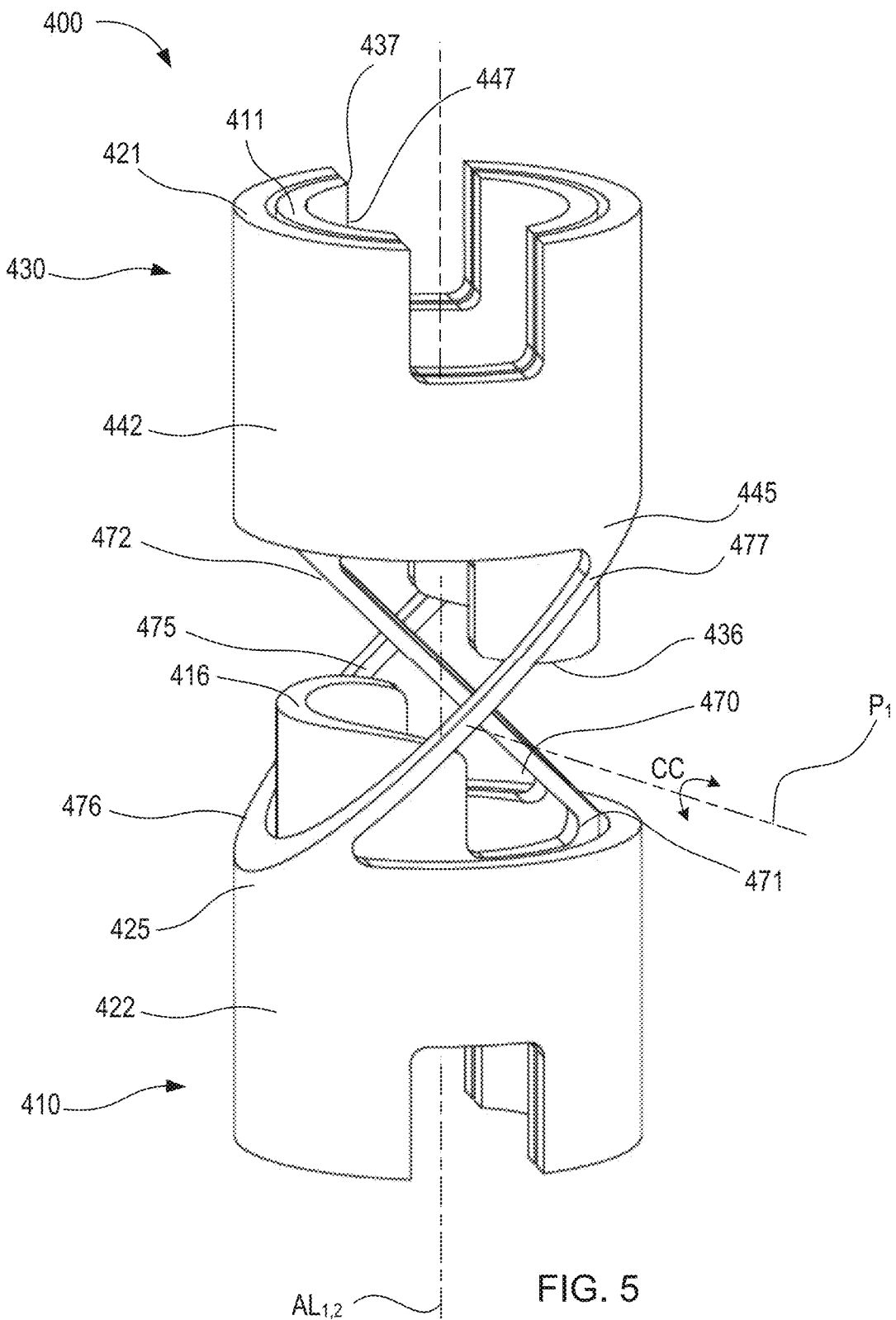
FIGS. 5 and 6 are perspective views of a compliant joint mechanism, according to an embodiment.
Figure 6:
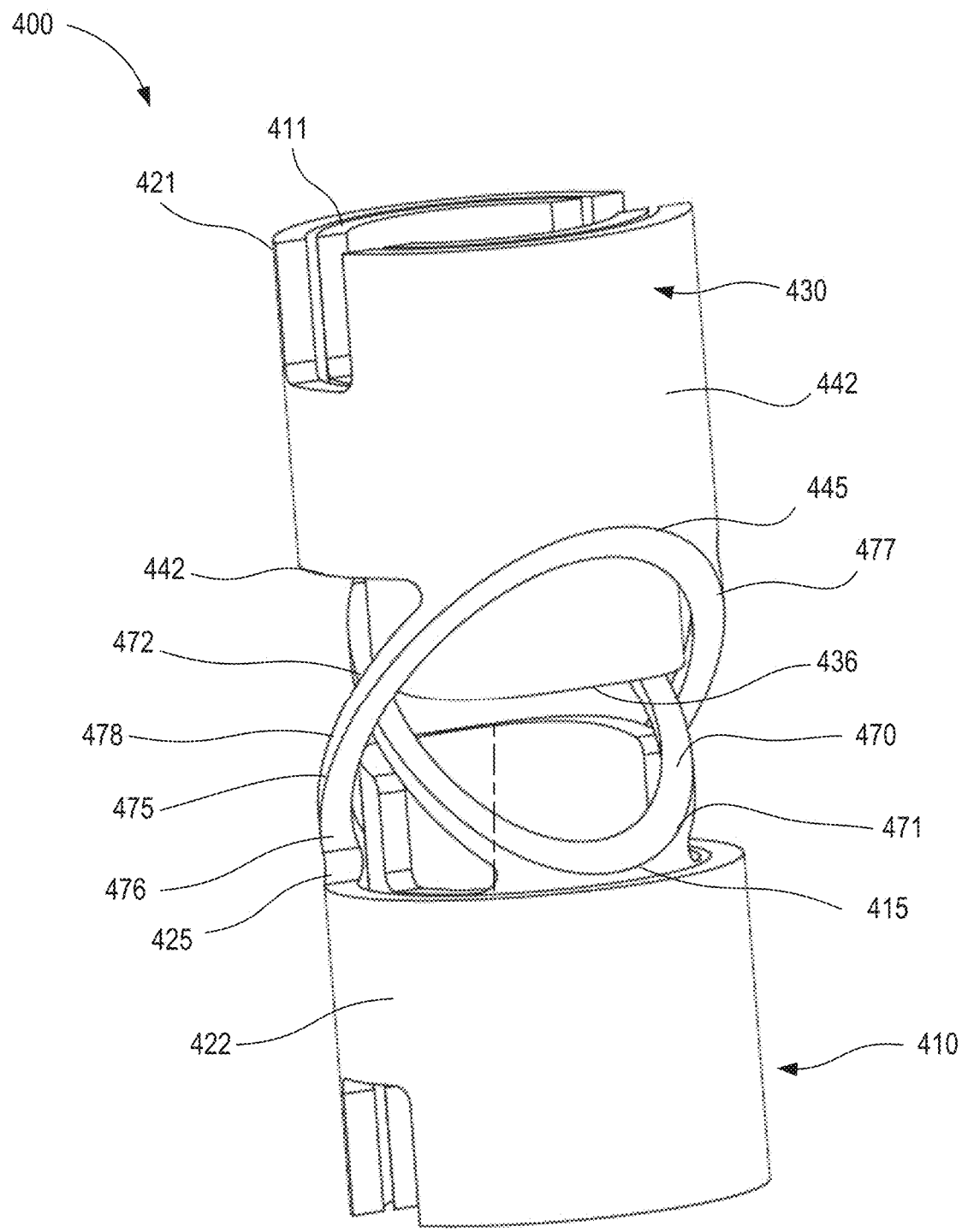
Figure 10:
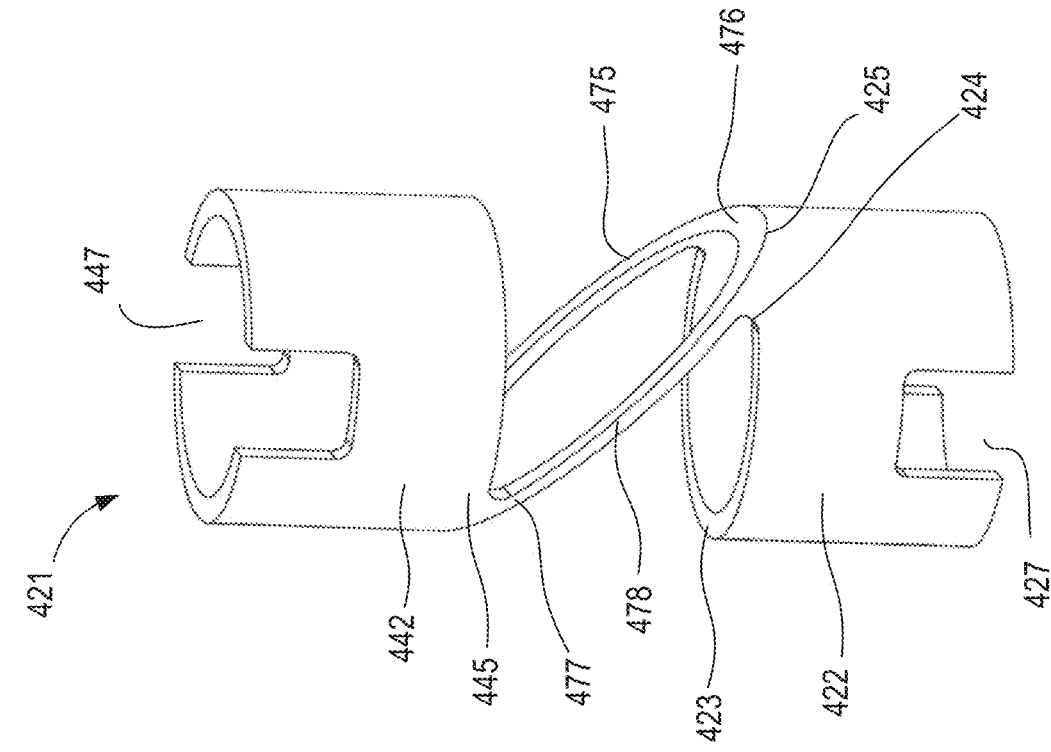
FIG. 10 is a perspective view of an inner member of the compliant joint mechanism shown in FIGS. 5 and 6.

Specifically, the joint assembly 400 is constructed from an inner cylinder 411 (FIGS. 7-9) and an outer cylinder 421 (FIGS. 10-12). As described in more detail below, the first joint member 410 includes a first end portion 412 of the inner cylinder 411 and a first end portion 422 of the outer cylinder 421. The second joint member 430 includes a second end portion 432 of the inner cylinder 411 and a second end portion 442 of the outer cylinder 421. In this manner, when the inner cylinder 411 is disposed within (and coupled to) the outer cylinder 421, as shown in FIGS. 5 and 6, the corresponding portions of the inner cylinder 411 and the outer cylinder 421 form the first joint member 410 and the second joint member coupled together by the flexures 470, 475.

Figure 8:
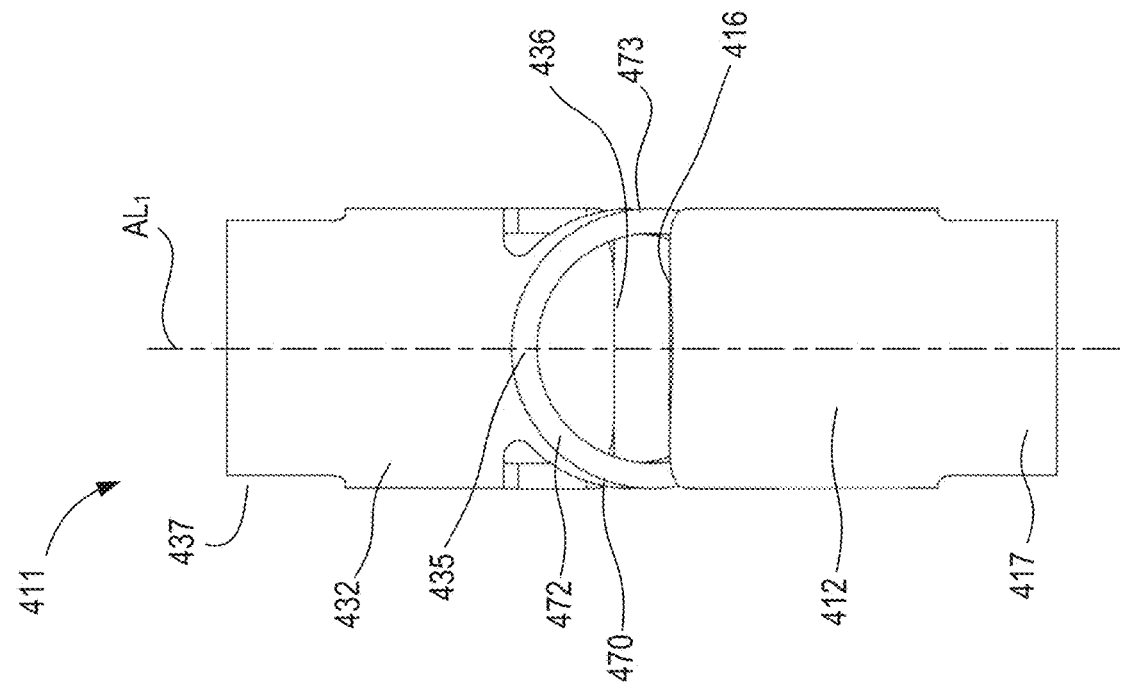
FIGS. 8 and 9 are a side view and a front view, respectively, of the inner member of the compliant joint mechanism shown in FIG. 7.
Figure 7:
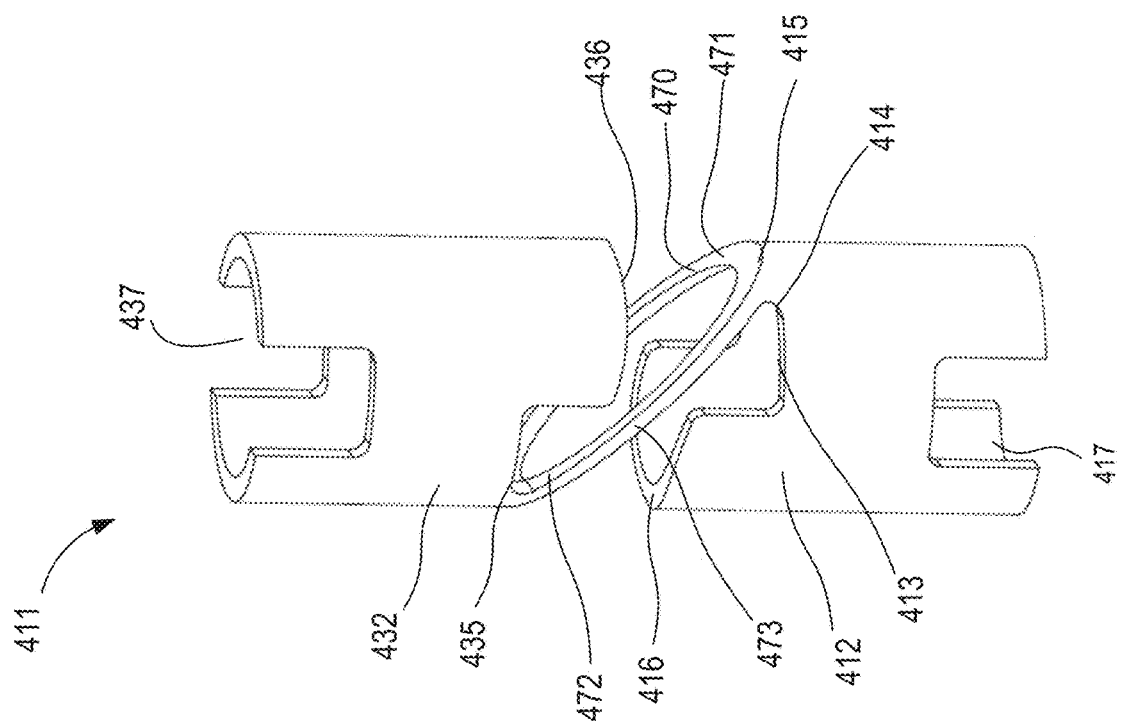
FIG. 7 is a perspective view of an inner member of the compliant joint mechanism shown in FIGS. 5 and 6.
Figure 9:
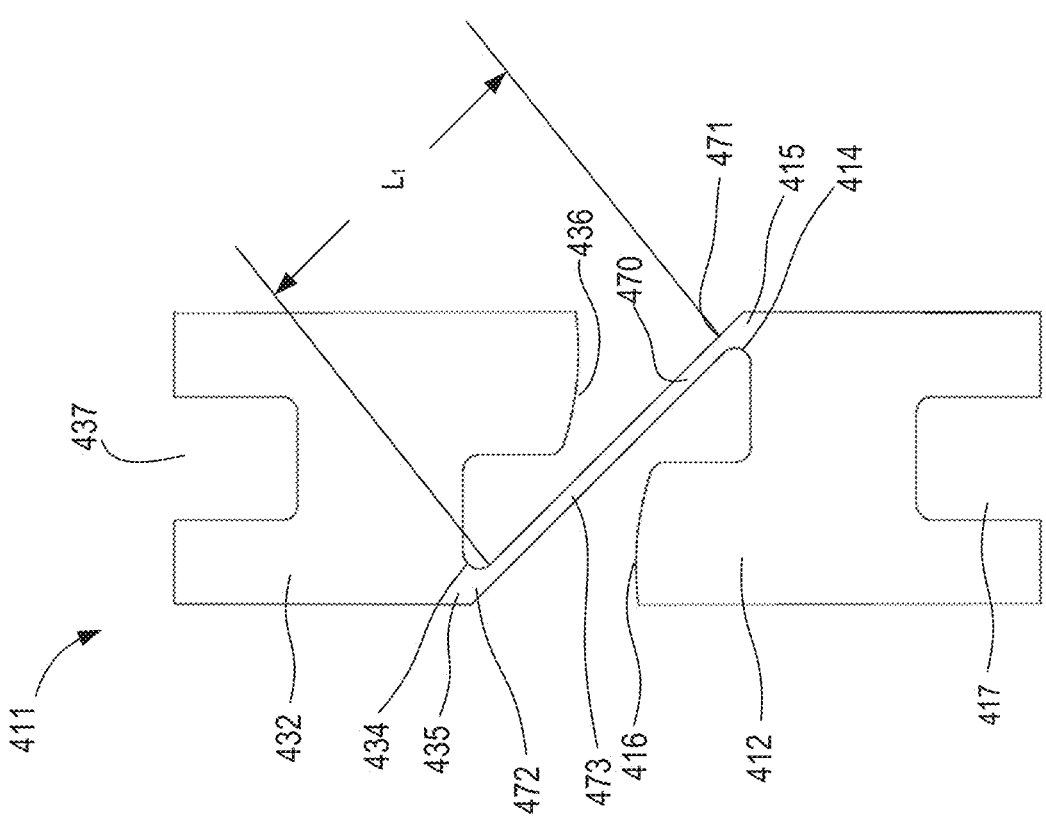

Referring to FIGS. 7-9, the inner cylinder 411 includes the first end portion 412, the second end portion 432, and the first flexure 470 coupled between the first end portion 412 and the second end portion 432. The inner cylinder 411 defines a first axis $AL_1$ (see FIG. 5) that is a longitudinal center line of the inner cylinder 411. Similarly stated, the first axis $AL_1$ is along the center points of the circular cross-sections of the inner cylinder 411. The first end portion 412 includes a connection portion 415 and a contact surface 416, and defines an alignment notch 417. The connection portion 415 includes a planar surface 413 that is substantially normal to the first axis $AL_1$, and can have any suitable properties to couple the first end portion 412 to the first (or inner) flexure 470. As shown in FIG. 9, the connection portion 415 includes a fillet 414 that smoothly transitions between the first end portion 412 and the first flexure 470. The fillet 414 (and the corresponding fillet 434 on the second end portion 432) are sized such that the first flexure 470 has a length $L_1$.

The connection portion 415 can be coupled to the first flexure 470 in any suitable manner. For example, in some embodiments, the connection portion 415 can be a surface (i.e., a connection surface) to which the first flexure 470 is joined (e.g., via welding, adhesive, or the like). In other embodiments, the connection portion 415 can include a protrusion, a recess, a fastener, or any other suitable fastening mechanism. In yet other embodiments, the connection portion 415 can be monolithically formed (i.e., can be integrally formed with) the first flexure 470. For example, in some embodiments, the inner cylinder 411 can be monolithically formed according to the method 10 shown and described herein.

The contact surface 416 can be any suitable surface that contacts the first flexure 470 during use. Although shown as being a curved surface, in other embodiments, the contact surface 416 can be a planar surface. In other embodiments, the contact surface 416 can have a specific profile or shape. For example, in some embodiments, the contact surface 416 can define a radius of curvature selected to control the bending of the first flexure 470 during use.

The second end portion 432 includes a connection portion 435 and a contact surface 436, and defines an alignment notch 437. The connection portion 435 includes a planar surface that opposes the planar surface 413, and that is substantially normal to the first axis $AL_1$. The connection portion 435 can have any suitable properties to couple the second end portion 432 to the first flexure 470. As shown in FIG. 9, the connection portion 435 includes a fillet 434 that smoothly transitions between the second end portion 432 and the first flexure 470. The connection portion 435 can be coupled to the first flexure 470 in any suitable manner. For example, in some embodiments, the connection portion 435 can be a surface (i.e., a connection surface) to which the first flexure 470 is joined (e.g., via welding, adhesive, or the like). In other embodiments, the connection portion 435 can include a protrusion, a recess, a fastener, or any other suitable fastening mechanism. In yet other embodiments, the connection portion 435 can be monolithically formed (i.e., can be integrally formed with) the first flexure 470.

The contact surface 436 can be any suitable surface that contacts the first flexure 470 during use. Although shown as being a curved surface, in other embodiments, the contact surface 436 can be a planar surface. In other embodiments, the contact surface 436 can have a specific profile or shape. For example, in some embodiments, the contact surface 436 can define a radius of curvature selected to control the bending of the first flexure 470 during use.

Referring to FIGS. 10-12, the outer cylinder 421 includes the first end portion 422, the second end portion 442, and the second flexure 475 coupled between the first end portion 422 and the second end portion 442. The outer cylinder 421 defines a second axis $AL_2$ (see FIG. 5) that is a longitudinal center line of the outer cylinder 421. Similarly stated, the second axis $AL_2$ is along the center points of the circular cross-sections of the outer cylinder 421. The first end portion 422 includes a connection portion 425 and defines an alignment notch 427. The connection portion 425 includes a planar surface 423 that is substantially normal to the second axis $AL_2$, and can have any suitable properties to couple the first end portion 422 to the second (or outer) flexure 475. As shown in FIG. 12, the connection portion 425 includes a fillet 424 that smoothly transitions between the first end portion 422 and the second flexure 475. The fillet 424 (and the corresponding fillet 444 on the second end portion 442) are sized such that the second flexure 475 has a length $L_2$. In some embodiments, the fillets are sized such that the length $L_1$ of the first flexure 470 is substantially equal to the length $L_2$ of the second flexure 475.

The connection portion 425 can be coupled to the second flexure 475 in any suitable manner. For example, in some embodiments, the connection portion 425 can be a surface (i.e., a connection surface) to which the second flexure 475 is joined (e.g., via welding, adhesive, or the like). In other embodiments, the connection portion 425 can include a protrusion, a recess, a fastener, or any other suitable fastening mechanism. In yet other embodiments, the connection portion 425 can be monolithically formed (i.e., can be integrally formed with) the second flexure 475. For example, in some embodiments, the outer cylinder 421 can be monolithically formed according to the method 10 shown and described herein.

The second end portion 442 includes a connection portion 445 and defines an alignment notch 447. The connection portion 445 includes a planar surface that opposes the planar surface 423, and that is substantially normal to the second axis $AL_2$. The connection portion 445 can have any suitable properties to couple the second end portion 442 to the second flexure 475. As shown in FIG. 12, the connection portion 445 includes a fillet 444 that smoothly transitions between the second end portion 442 and the second flexure 475. The connection portion 445 can be coupled to the second flexure 475 in any suitable manner. For example, in some embodiments, the connection portion 445 can be a surface (i.e., a connection surface) to which the second flexure 475 is joined (e.g., via welding, adhesive, or the like). In other embodiments, the connection portion 445 can include a protrusion, a recess, a fastener, or any other suitable fastening mechanism. In yet other embodiments, the connection portion 445 can be monolithically formed (i.e., can be integrally formed with) the second flexure 475.

The first joint member 410 is coupled to the second joint member 430 via the first (or inner) flexure 470 and the second (or outer) flexure 475. The first flexure 470 has a first end portion 471, a second end portion 472, and a central portion 473 between the first end portion 471 and the second end portion 472. The first end portion 471 is coupled to the connection portion 415 of the inner cylinder 411, and the second end portion 472 is coupled to the connection portion 435 of the inner cylinder 411, as described above. The second flexure 475 has a first end portion 476, a second end portion 477, and a central portion 478 between the first end portion 476 and the second end portion 477. The first end portion 476 is coupled to the connection portion 425 of the outer cylinder 421, and the second end portion 477 is coupled to the connection portion 445 of the outer cylinder 421.

In use, the first flexure 470 and the second flexure 475 each deform elastically when the second joint member 430 moves relative to the first joint member 410. Similarly stated, the first flexure 470 and the second flexure 475 deform elastically when the first joint member 410 and the second joint member 430 move from a first configuration (FIG. 3) to a second configuration (not shown). Thus, the flexures are resilient members that store energy from an actuation force and releases the energy when the actuation force is removed, thus allowing the joint assembly 400 to repeatedly be moved between the various configurations.

When the joint assembly 400 transitions from the first configuration to the second configuration, the second joint member 430 rotates relative to the first joint member 410, as shown by the arrow CC in FIG. 5. In particular, the second joint member 430 rotates relative to the first joint member 410 about an axis of rotation (also referred to as a pivot axis), indicated by $P_1$. The axis of rotation $P_1$ can be approximated as the axis at which the first flexure 470 crosses the second flexure 475 when the joint assembly 400 is in the first configuration. As shown in FIG. 5, the first axis $AL_1$ and the second axis $AL_2$ intersect, and are substantially normal to, the axis of rotation $P_1$. Moreover, in some embodiments the length of the flexures (the length $L_1$ and the length $L_2$) are substantially equal. In such embodiments, the axis of rotation $P_1$ can be approximated as being at a substantially constant location relative to the first joint member 410 during movement of the second joint member 430. In other embodiments, however, a joint assembly can be configured such that the axis of rotation $P_1$ is spaced apart from an axis at which the flexures cross, or the axis of rotation $P_1$ translates when the joint assembly transitions from the first configuration to the second configuration.

When the joint assembly 400 is in the first configuration (FIGS. 5 and 6), the central portion 473 of the first flexure 470 is spaced apart from the contact surfaces 416, 436. When the joint assembly 400 is in a second configuration (not shown), the second joint member 430 rotates counter-clockwise relative to the first joint member 410, and the central portion 473 of the first flexure 470 contacts the contact surface 416. In this manner, the contact surface 416 can control the deformation of the first flexure 470. Similarly stated, the engagement between the contact surface 416 and the central portion 473 of the first flexure 470 when the first joint member 410 and the second joint member 430 move from the first configuration to the second configuration constrains the radius of curvature of the first flexure 470. This can, in turn, limit the stress in the first flexure 470 and maintain a substantially constant stress during the deformation of the first flexure 470. When the joint assembly 400 moves to a third configuration (not shown), the second joint member 430 rotates clockwise relative to the first joint member 410, and the central portion 473 of the first flexure 470 contacts the contact surface 436. In this manner, the contact surface 436 can control the deformation of the first flexure 470, as described above.

Although not shown in FIGS. 5 and 12, the force to move the second joint member 430 relative to the first joint member 410 (referred to as the actuation force) can be applied to any suitable portion of the joint assembly 400 by any suitable mechanism. For example, in some embodiments, the second joint member 430 can include an engagement portion that receives the actuation force to transition the joint assembly 400 between the various configurations. In some embodiments, the actuation force can be applied via a flexible cable or a rigid rod at a fixed point on the second joint member 430. In other embodiments, the actuation force can be applied via a flexible cable or a rigid rod at multiple points on the second joint member 430. Moreover, the hollow, cylindrical shape of the joint assembly 400 allows the actuation members (e.g., rods, cables, or the like) to be disposed within the inner cylinder 411 of the joint assembly 400. In this manner, the outer surface of the joint assembly 400 can be devoid of moving cables, external rods, or other actuation members that can cause an increased size.

Although the joint assembly 400 is shown as including the inner cylinder 411 having contact surfaces 416, 436 and the outer cylinder 421 being devoid of contact surfaces, in other embodiments, any joint member (or cylinder) can include any suitable number of contact surfaces. Such contact (or cam) surfaces can selectively contact a portion of the flexures to constrain the radius of curvature of the flexure, control the deformation of the flexure, maintain a desired stress in the flexure during bending, or the like—as described herein. For example, in some embodiments, a cylindrical joint assembly can include two nested cylinders that each include contact surfaces. Specifically, FIGS. 13-16 are various views of a joint assembly 500 according to an embodiment. The joint assembly 500 includes a first joint member 510 and a second joint member 530 that are movably coupled together by a first flexure 470 and a second flexure 575. The joint assembly 500, and any of the joint assemblies described herein, can be used in any suitable surgical device or system as described herein. For example, the joint assembly 500 or any of the components therein are optionally parts of an end effector (such as a gripper, shears, or the like), an articulating shaft, a wrist assembly, or the like. Either of the first joint member 510 or the second joint member 530 can be coupled to an end of a surgical instrument shaft to form a wrist assembly that allows the end effector to change orientation (e.g., one or more of roll, pitch, and yaw) with reference to the shaft.

Figure 13:
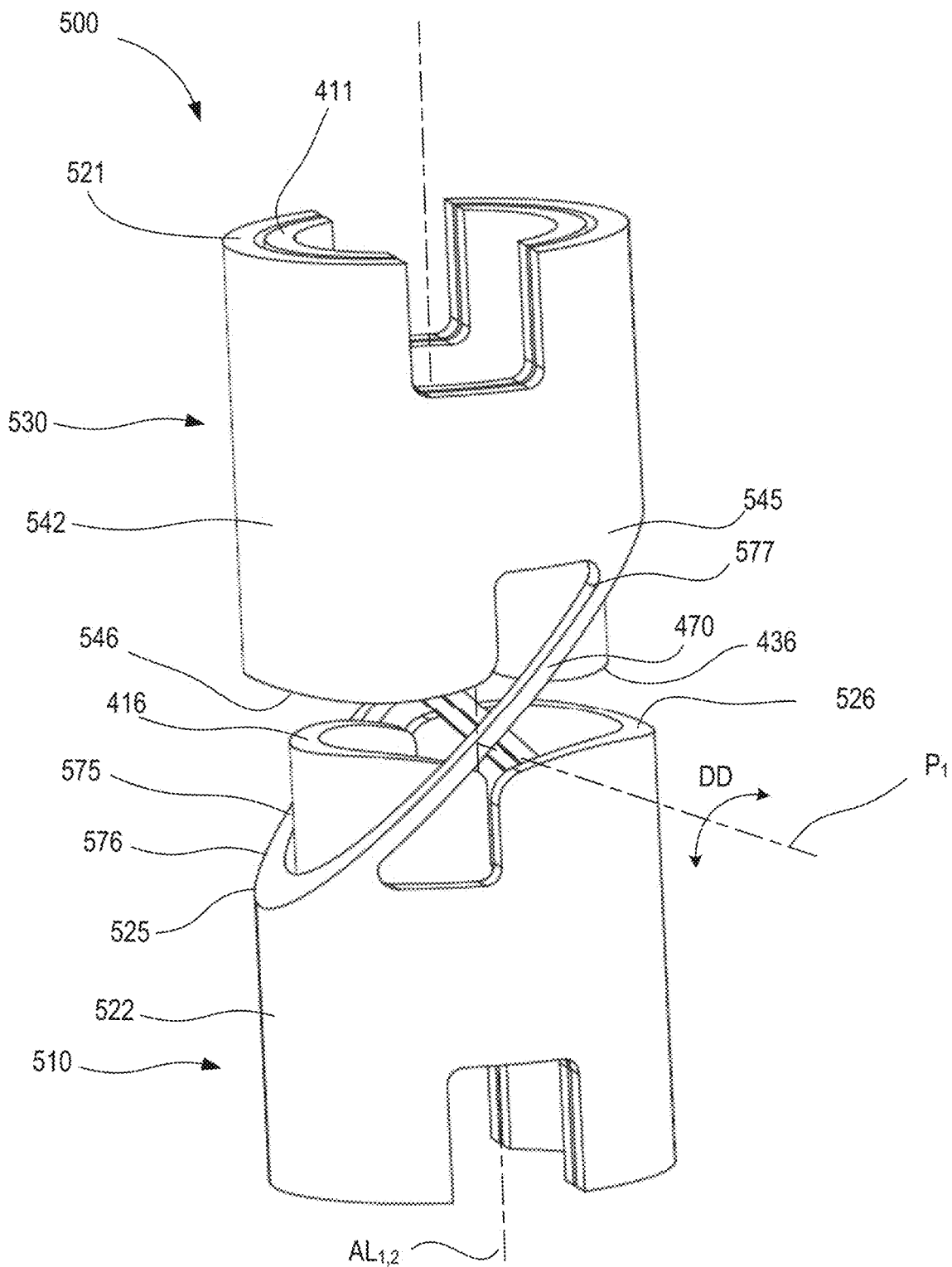
FIGS. 13 and 14 are perspective views of a compliant joint mechanism, according to an embodiment.
Figure 14:
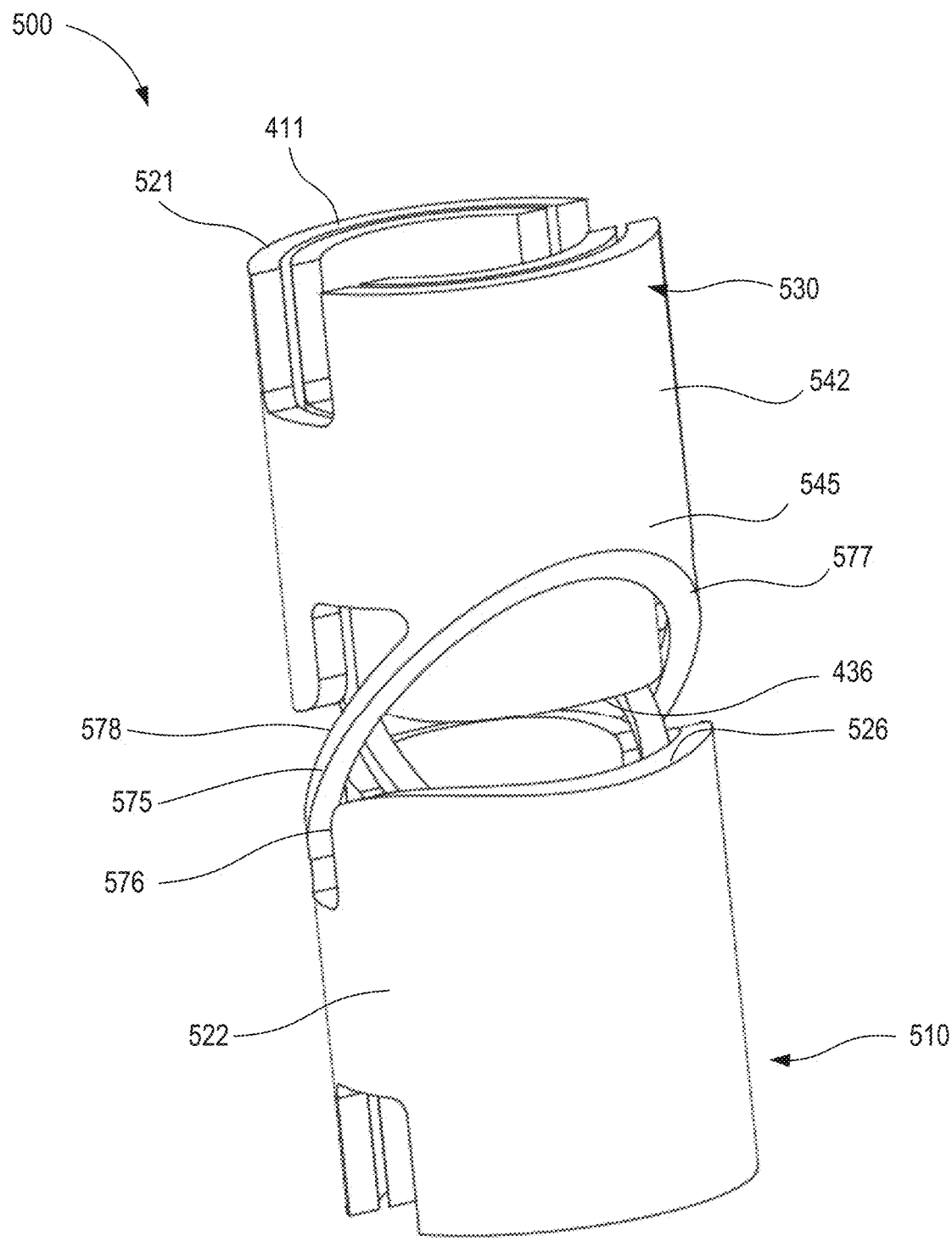

Specifically, the joint assembly 500 is constructed from an inner cylinder 411 (see FIGS. 7-9) and an outer cylinder 521 (see FIGS. 15-16). As described in more detail below, the first joint member 510 includes the first end portion 412 of the inner cylinder 411 and a first end portion 522 of the outer cylinder 521. The second joint member 530 includes the second end portion 432 of the inner cylinder 411 and a second end portion 542 of the outer cylinder 521. In this manner, when the inner cylinder 411 is disposed within (and coupled to) the outer cylinder 521, as shown in FIGS. 13 and 14, the corresponding portions of the inner cylinder 411 and the outer cylinder 521 form the first joint member 510 and the second joint member coupled together by the flexures 470, 575.

The inner cylinder 421 is the same as that described above for the joint assembly 400, and is therefore not described in detail below. Referring to FIGS. 15-16, the outer cylinder 521 includes the first end portion 522, the second end portion 542, and the second flexure 575 coupled between the first end portion 522 and the second end portion 542. The outer cylinder 521 defines a second axis $AL_2$ (see FIG. 13) that is a longitudinal center line of the outer cylinder 521. Similarly stated, the second axis $AL_2$ is along the center points of the circular cross-sections of outer cylinder 521. The first end portion 522 includes a connection portion 525 and a contact surface 526, and defines an alignment notch 527. The connection portion 525 includes a planar surface that is substantially normal to the second axis $AL_2$, and can have any suitable properties to couple the first end portion 522 to the second (or outer) flexure 575. As shown in FIG. 16, the connection portion 525 includes a fillet 524 that smoothly transitions between the first end portion 522 and the second flexure 575. The fillet 524 (and the corresponding fillet 544 on the second end portion 542) are sized such that the second flexure 575 has a length that is substantially equal to the length $L_1$ of the first flexure 470. In other embodiments, however, the fillets are sized such that the length $L_1$ of the first flexure 470 is different than the length of the second flexure 575.

The connection portion 525 can be coupled to the second flexure 575 in any suitable manner. For example, in some embodiments, the connection portion 525 can be a surface (i.e., a connection surface) to which the second flexure 575 is joined (e.g., via welding, adhesive, or the like). In other embodiments, the connection portion 525 can include a protrusion, a recess, a fastener, or any other suitable fastening mechanism. In yet other embodiments, the connection portion 525 can be monolithically formed (i.e., can be integrally formed with) the second flexure 575. For example, in some embodiments, the outer cylinder 521 can be monolithically formed according to the method 10 shown and described herein.

The contact surface 526 can be any suitable surface that contacts the second flexure 575 during use. Although shown as being a curved surface, in other embodiments, the contact surface 526 can be a planar surface. In other embodiments, the contact surface 526 can have a specific profile or shape. For example, in some embodiments, the contact surface 526 can define a radius of curvature selected to control the bending of the second flexure 575 during use.

The second end portion 542 includes a connection portion 545 and a contact surface 546, and defines an alignment notch 547. The connection portion 545 includes a planar surface that opposes the planar surface of the first end portion 522, and that is substantially normal to the second axis $AL_2$. The connection portion 545 can have any suitable properties to couple the second end portion 542 to the second flexure 575. As shown in FIG. 16, the connection portion 545 includes a fillet 544 that smoothly transitions between the second end portion 542 and the second flexure 575. The connection portion 545 can be coupled to the second flexure 575 in any suitable manner. For example, in some embodiments, the connection portion 545 can be a surface (i.e., a connection surface) to which the second flexure 575 is joined (e.g., via welding, adhesive, or the like). In other embodiments, the connection portion 545 can include a protrusion, a recess, a fastener, or any other suitable fastening mechanism. In yet other embodiments, the connection portion 545 can be monolithically formed (i.e., can be integrally formed with) the second flexure 575.

The contact surface 546 can be any suitable surface that contacts the second flexure 575 during use. Although shown as being a curved surface, in other embodiments, the contact surface 546 can be a planar surface. In other embodiments, the contact surface 546 can have a specific profile or shape. For example, in some embodiments, the contact surface 546 can define a radius of curvature selected to control the bending of the second flexure 575 during use.

The first joint member 510 is coupled to the second joint member 530 via the first (or inner) flexure 470 and the second (or outer) flexure 575. The first flexure 470 is the same as the first flexure 470 describe above with respect to the joint assembly 400. The second flexure 575 has a first end portion 576, a second end portion 577, and a central portion 578 between the first end portion 576 and the second end portion 577. The first end portion 576 is coupled to the connection portion 525 of the outer cylinder 521, and the second end portion 577 is coupled to the connection portion 545 of the outer cylinder 521.

In use, the first flexure 470 and the second flexure 575 each deform elastically when the second joint member 530 moves relative to the first joint member 510. Similarly stated, the first flexure 470 and the second flexure 575 deform elastically when the first joint member 510 and the second joint member 530 move from a first configuration (FIGS. 13 and 14) to a second configuration or third configuration (not shown). Thus, the flexures are resilient members that store energy from an actuation force and releases the energy when the actuation force is removed, thus allowing the joint assembly 500 to repeatedly be moved between the various configurations.

When the joint assembly 500 transitions from the first configuration to the second configuration, the second joint member 530 rotates relative to the first joint member 510, as shown by the arrow DD in FIG. 13. In particular, the second joint member 530 rotates relative to the first joint member 510 about an axis of rotation (also referred to as a pivot axis), indicated by $P_1$. The axis of rotation $P_1$ can be approximated as the axis at which the first flexure 470 crosses the second flexure 575 when the joint assembly 500 is in the first configuration. As shown in FIG. 13, the first axis $AL_1$ and the second axis $AL_2$ intersect, and are substantially normal to, the axis of rotation $P_1$. Moreover, in some embodiments the length of the flexures is substantially equal. In such embodiments, the axis of rotation $P_1$ can be approximated as being at a substantially constant location relative to the first joint member 510 during movement of the second joint member 530. In other embodiments, however, a joint assembly can be configured such that the axis of rotation $P_1$ is spaced apart from an axis at which the flexures cross, or the axis of rotation $P_1$ translates when the joint assembly transitions from the first configuration to the second configuration.

When the joint assembly 500 is in the first configuration (FIGS. 13 and 14), the central portion of the first flexure 470 is spaced apart from the contact surfaces 416, 436, and the central portion 578 of the second flexure 575 is spaced apart from the contact surfaces 526, 546. When the joint assembly 500 is moved to a second configuration (not shown), the second joint member 530 rotates counter-clockwise relative to the first joint member 510, and the central portion of the first (inner) flexure 470 contacts the contact surface 416. Additionally, the central portion 578 of the second (outer) flexure 575 contacts the contact surface 546. In this manner, the contact surface 516 and the contact surface 546 can control the deformation of the first flexure 470 and the second flexure 575, respectively. Similarly stated, the engagement between the contact surface 416 and the central portion of the first flexure 470 when the first joint member 510 and the second joint member 530 move from the first configuration to the second configuration constrains the radius of curvature of the first flexure 470. The engagement between the contact surface 546 and the central portion 578 of the second flexure 575 when the first joint member 510 and the second joint member 530 move from the first configuration to the second configuration constrains the radius of curvature of the second flexure 575. This can, in turn, limit the stress in the first flexure 470 and the second flexure 575, and maintain a substantially constant stress during the deformation of the flexures.

When the joint assembly 500 moves to a third configuration (not shown), the second joint member 530 rotates clockwise relative to the first joint member 510. The central portion of the first flexure 470 contacts the contact surface 436 and the central portion 578 of the second flexure 575 contacts the contact surface 526. In this manner, the contact surfaces 526, 436 can control the deformation of the second flexure 575 and the first flexure 470, respectively. Similarly stated, the engagement between the contact surface 526 and the central portion 578 of the second flexure 575 when the first joint member 510 and the second joint member 530 move from the first configuration to the third configuration constrains the radius of curvature of the second flexure 575. The engagement between the contact surface 436 and the central portion of the first flexure 470 when the first joint member 510 and the second joint member 530 move from the first configuration to the third configuration constrains the radius of curvature of the first flexure 470. This can, in turn, limit the stress in the flexures and maintain a substantially constant stress during the deformation of the flexures.

Although not shown in FIGS. 13 and 14, the force to move the second joint member 530 relative to the first joint member 510 (referred to as the actuation force) can be applied to any suitable portion of the joint assembly 500 by any suitable mechanism. For example, in some embodiments, the second joint member 530 can include an engagement portion that receives the actuation force to transition the joint assembly 500 between the various configurations. In some embodiments, the actuation force can be applied via a flexible cable or a rigid rod at a fixed point on the second joint member 530. In other embodiments, the actuation force can be applied via a flexible cable or a rigid rod at multiple points on the second joint member 530. Moreover, the hollow, cylindrical shape of the joint assembly 500 allows the actuation members (e.g., rods, cables, or the like) to be disposed within the inner cylinder 411 of the joint assembly 500. In this manner, the outer surface of the joint assembly 500 can be devoid of moving cables, external rods, or other actuation members that can cause an increased size.

Controlling the curvature of the flexures for the cylindrical joint assembly 400 or the cylindrical joint assembly 500 (or any of the flexures described herein) can enable a larger angular deflection before the flexure yields. For the cylindrical cross-axis flexural design, the flexures are elliptical segments defined by the cylinder diameter and flexure angle. As a first approximation of the flexure length, the straight-line distance of the flexure based on the inner diameter is used. This approximation can be similar to or the same as the flexure lengths $L_1$ and $L_2$ shown and described above. Specifically, the straight-line approximation of the flexure length, L, is:

$$L \approx \frac{D_i}{\cos \beta} \quad (5)$$

Where Di is the inner diameter of the inner cylinder and β is the angle of the flexure from a plane cutting the cylinder orthogonal to the axis (e.g., the first axis $AL_1$ or the second axis $AL_2$) of the cylinder. The flexure length is constrained by the inner diameter of the inner cylinder. As described above, in some embodiments, the flexure in the outer cylinder is designed to be the same straight-line length as that for the inner cylinder to maintain approximate flexure symmetry. As described above, this can be achieved by adding a fillet (e.g., fillet 524 and fillet 524) with a larger radius to each side as compared to the fillets (e.g., fillet 414 and fillet 434) of the inner cylinder. The approximate length, L, can then be used to calculate the theoretical angular deflection, $\theta_{cam}$, as:

$$\theta_{cam} = \frac{2S_y L}{Eh} \quad \text{Eq. (6)}$$

Were Sy is the yield strength of the material, E is the modulus of elasticity, and h is the flexure thickness. Equations 3 and 6 were used to calculate the radius of curvature of the contact (or cam) surface for the steel prototypes, shown in FIGS. 17-19 and 21.

Due to the elliptical shape of the flexures for the cylindrical cross-axis design, the flexures (e.g., flexures 470, 475, and 575) are not in complete contact with the corresponding contact surfaces (e.g., contact surfaces 416, 436, 526, 546) during deflection. The moving platform of the mechanism, including a portion of the flexure, begins to exit the boundary defined by the cylinder surface and therefore does not engage the contact surface. If the flexure is rotated beyond this point it will yield (possibly leading to flexure failure if yielding is not desired). This issue is more apparent when the wall thickness of the cylinder is small compared to the cylinder diameter.

Figure 19:
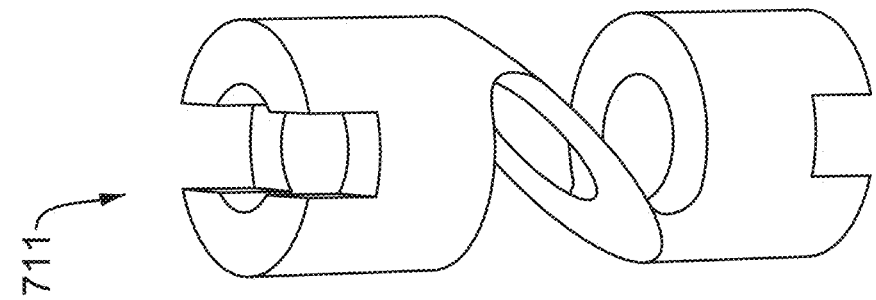
FIGS. 17-19 are photographs of a prototype compliant joint assembly, according to an embodiment.
Figure 18:
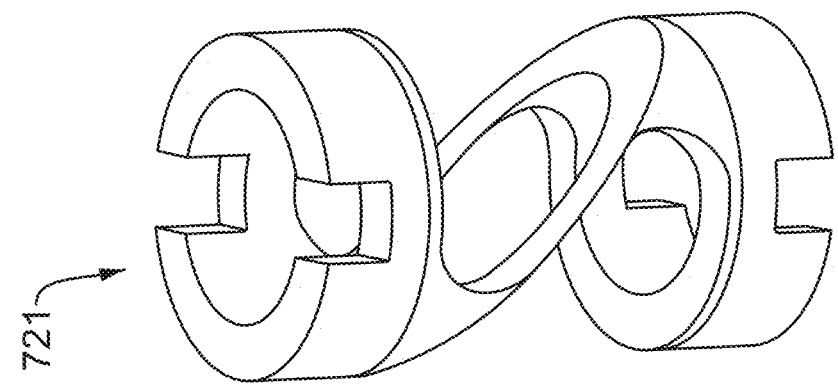
Figure 17:
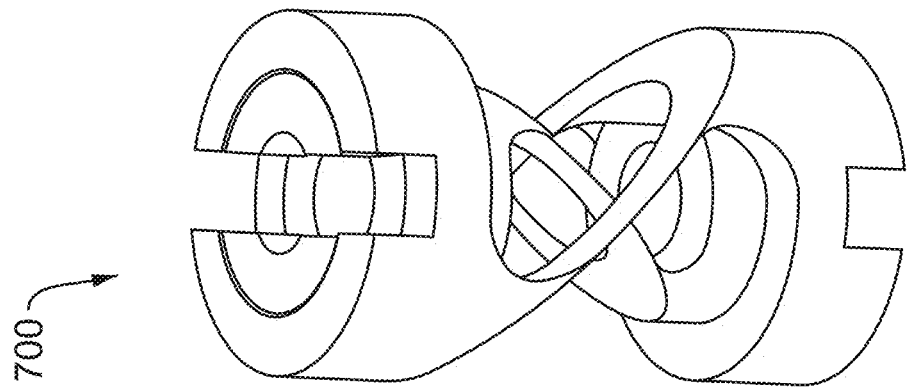

To evaluate the performance of the joint assembly 400 and the joint assembly 500, a series of physical prototype joint assemblies were made. As discussed below, the performance of the prototype joint assemblies was compared against both the analytical modeling described herein, and also against finite element modeling. Specifically, FIGS. 17-19 are photographs of a large-scale prototype compliant joint assembly 700 that was constructed from 4130 steel tubing. The cut pattern for the joint assembly 700 (and the joint assemblies 400, 500) is planar, and therefore lends itself to a wide variety manufacturing methods, including the method 10 described below, as well as a variety of material-removal methods, including laser-cutting, wire-EDM, waterjet, and traditional machining.

The joint assembly 700 includes an inner cylinder 711 and an outer cylinder 721. The inner cylinder 711 is similar in design and function to the inner cylinder 411 described above, but does not include the contact surfaces 416, 436. The outer cylinder 721 is similar to the outer cylinder 421 shown and described above. Thus, the joint assembly 700 can be considered a "no-cam" design, and serves as a baseline to which joint assemblies that include one or more contact surfaces can be compared. The alignment notches (similar to the alignment notches 417, 427, 437, 447 shown and described above with respect to the joint assembly 400) serve to facilitate circumferential alignment of the inner cylinder 711 and the outer cylinder 721 during assembly. In this manner, the inner cylinder 711 and the outer cylinder 721 can be circumferentially aligned (e.g., within less than 5 degrees). The dimensions of the joint assembly 700 are provided in Table 1.

TABLE 1

| Joint Assembly 700 Dimensions | | |
|---|---|---|
| Parameter | Inner Cylinder 711 | Outer Cylinder 721 |
| Outer diameter, OD (mm) | 19.05 | 28.58 |
| Inner diameter, ID (mm) | 9.50 | 19.02 |
| Wall thickness, WT (mm) | 4.78 | 4.78 |
| Flexure angle, FA (deg) | 45 | 45 |
| Flexure thickness, FT (mm) | 0.25 | .25 |
| Flexure length, FL (mm) | 13.72 | 13.46 |

Figure 20:
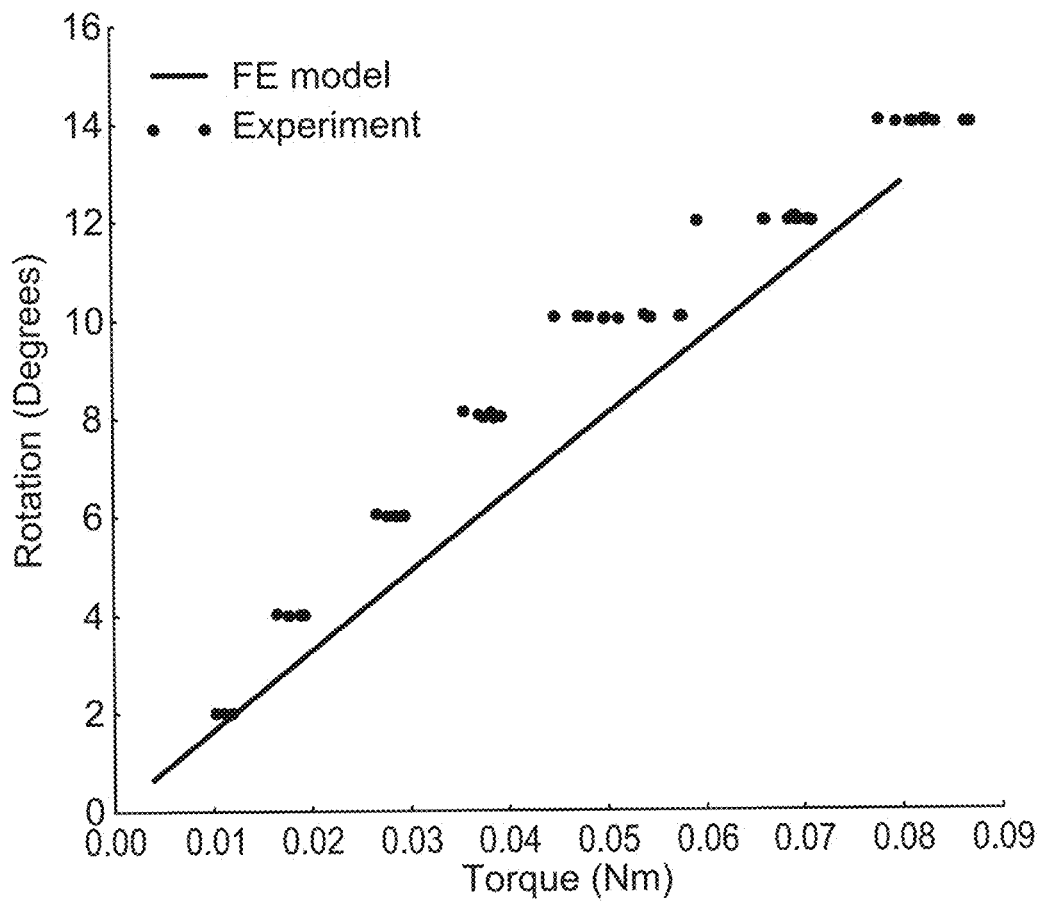
FIG. 20 is a plot of the angular deflection as a function of bending torque for the prototype shown in FIGS. 17-19, including measured data and finite element analysis data.

Experimental data was collected for the joint assembly 700, and was compared to finite element model data. In particular, the rotational torque and the resulting angle of deflection of the second joint member to the first joint member was evaluated. For the experimental data, a calibrated torque sensor measured the reaction moment as the joint assembly was deflected, and an optical encoder recorded the angle to which the joint assembly was deflected for each reaction-moment measurement. FIG. 20 is a plot of the angular deflection as a function of torque for the joint assembly 700.

Figure 21:
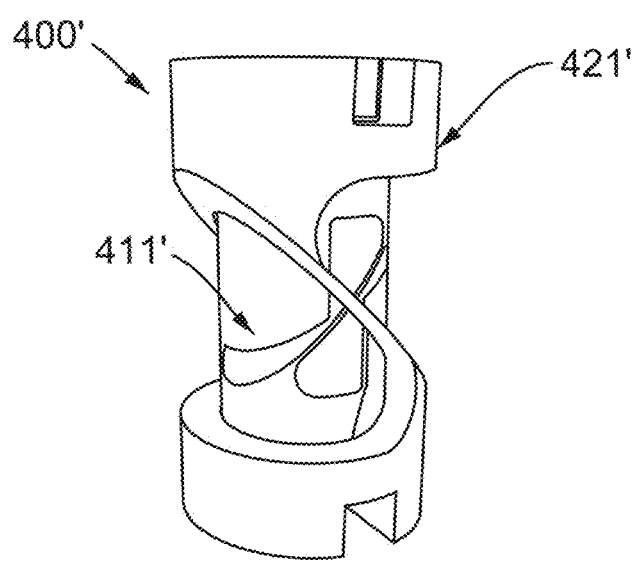
FIG. 21 is a photograph of a prototype compliant joint assembly, according to an embodiment.

FIG. 21 is a photograph of a large-scale prototype compliant joint assembly 400' that was constructed from 4130 steel tubing. The cut pattern for the joint assembly 400' (and the joint assemblies 400, 500) is planar, and therefore lends itself to a wide variety manufacturing methods, including the method 10 described below, as well as a variety of material-removal methods, including laser-cutting, wire-EDM, waterjet, and traditional machining.

The joint assembly 400' includes an inner cylinder 411', and an outer cylinder 421'. The inner cylinder 411' is similar in design and function to the inner cylinder 411 described above, and includes the contact surfaces 416, 436. The outer cylinder 421' is similar to the outer cylinder 421 shown and described above. Thus, the joint assembly 400' can be considered a "inner cylinder cam" design, and replicates the design of the joint assembly 400 described above. The dimensions of the joint assembly 400' are provided in Table 1.

Because the outer flexure is slightly longer than the inner flexure (due to the larger OD size), the highest stress will be developed in the inner flexure for a given deflection. Note that in Table 1 the flexure length is the straight-line approximation. Thus, when the elliptical shape of the flexure is considered the inner flexure will have a slightly shorter effective flexure length compared to the outer cylinder. Accordingly, by limiting the stress on the inner flexure the highest stress of the mechanism will be limited. Thus, the contact (or cam) surfaces for the joint assembly 400' (and the joint assembly 400) are provided on the inner cylinder. In other embodiments, such as the joint assembly 500, the contact (or cam) surfaces could also be located on the outer cylinder.

Figure 22:
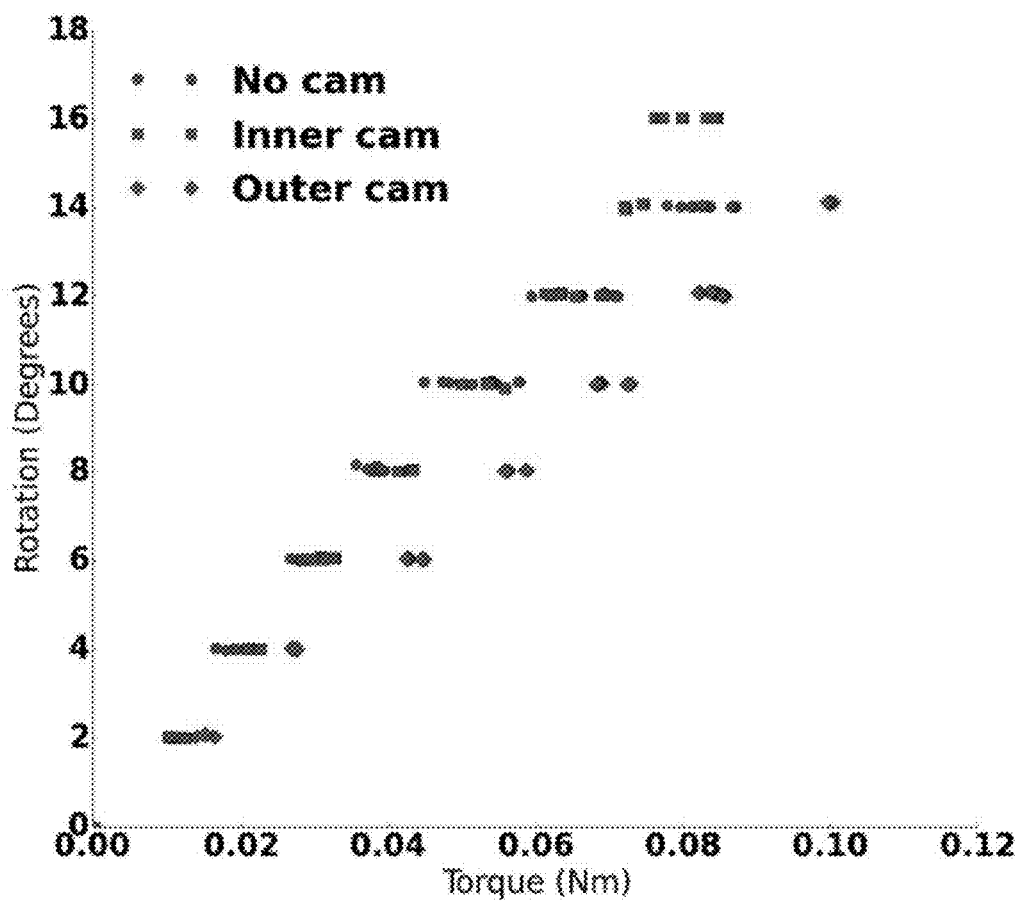
FIG. 22 is a plot of the angular deflection as a function of bending torque for the prototype shown in FIG. 21, in comparison with other embodiments.

FIG. 22 is a plot of the angular deflection as a function of torque for the joint assembly 400' compared to that for the joint assembly 700 (the "no cam" design) and a prototype joint assembly similar to the joint assembly 500 (a "outer cam" design). As shown, there is a difference in stiffness between the prototype with the cam-surfaces on the outside cylinder and the prototype joint assembly 700 without contact (or cam) surfaces. It is expected that the introduction of contact (or cam) surfaces may modify the mechanism stiffness because the flexure curvature is constrained. The data from the prototype with contact (or cam) surfaces on the inner cylinder closely matches the data from the prototype joint assembly 700 without cam-surfaces.

Although the joint assembly 400, the joint assembly 500, and other joint assemblies are shown and described herein as having a single axis of rotation, which allows for a single degree of freedom, in other embodiments, a joint assembly can include multiple degrees of freedom. For example, in some embodiments, a cylindrical joint assembly, similar to the joint assembly 400 or the joint assembly 500, but with an additional set of flexures, which allows for two degrees of freedom of the joint assembly. In some embodiments, the joint assembly can be configured such that a first axis of rotation and a second axis of rotation intersect. This arrangement can reduce the overall length of the joint assembly by allowing multiple degrees of freedom at a single longitudinal point along the joint assembly. As one example, FIGS. 23-32 are various views of a joint assembly 600 according to an embodiment. The joint assembly 600 includes a first joint member 610, a second joint member 630, and a third joint member 650 that are movably coupled together by a series of flexures. The third joint member 650 is between the first joint member 610 and the second joint member 630 and, as described herein, allows the second joint member 630 to rotate relative to the first joint member 610 about two different axes. The joint assembly 600, and any of the joint assemblies described herein, can be used in any suitable surgical device or system as described herein. For example, the joint assembly 600 or any of the components therein are optionally parts of an end effector (such as a gripper, shears, or the like), an articulating shaft, a wrist assembly, or the like. Either of the first joint member 610 or the second joint member 630 can be coupled to an end of a surgical instrument shaft to form a wrist assembly that allows the end effector to change orientation (e.g., one or more of roll, pitch, and yaw) with reference to the shaft.

Figure 23:
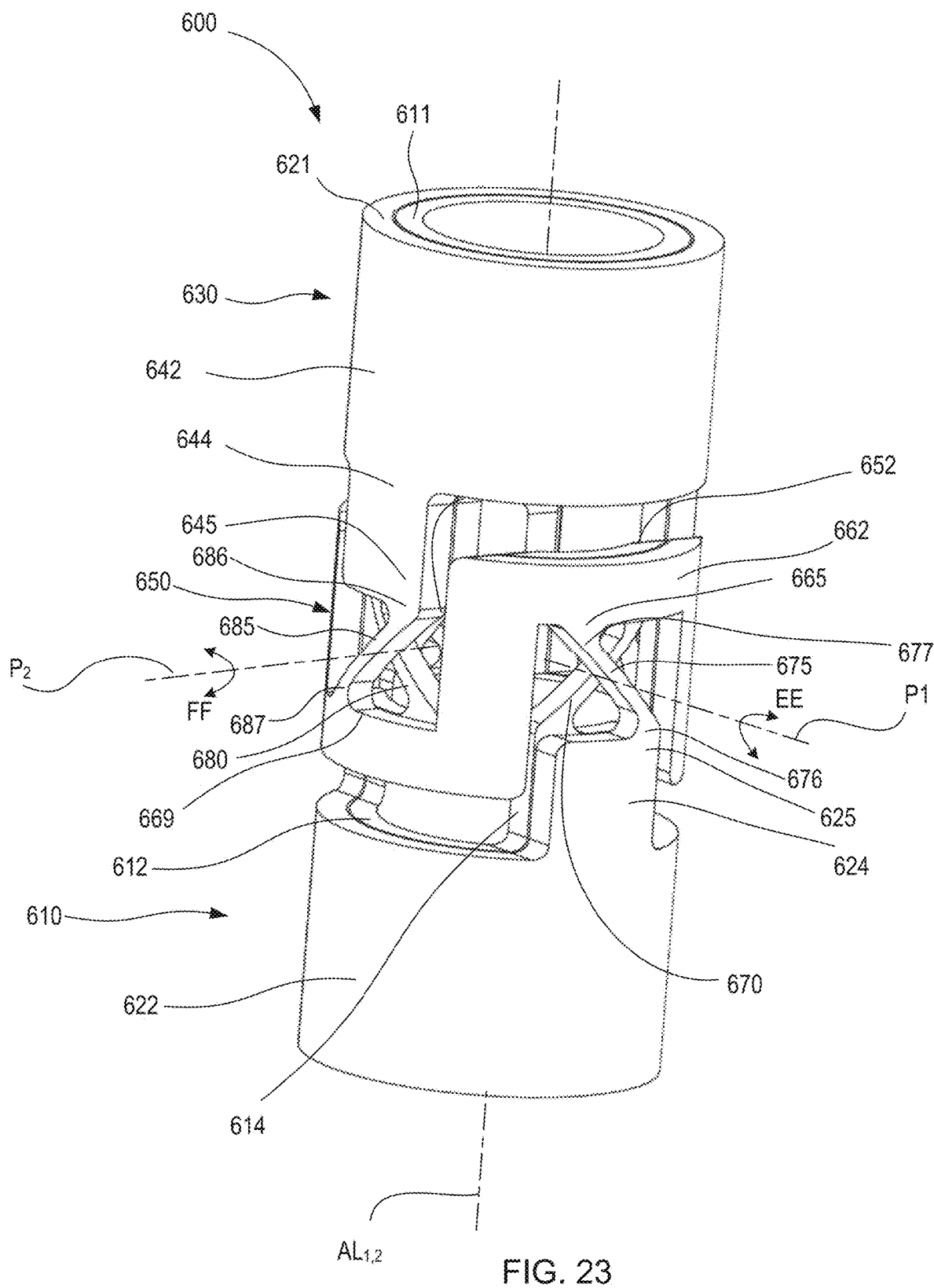
FIGS. 23 and 24 are perspective views of a compliant joint mechanism, according to an embodiment.
Figure 24:
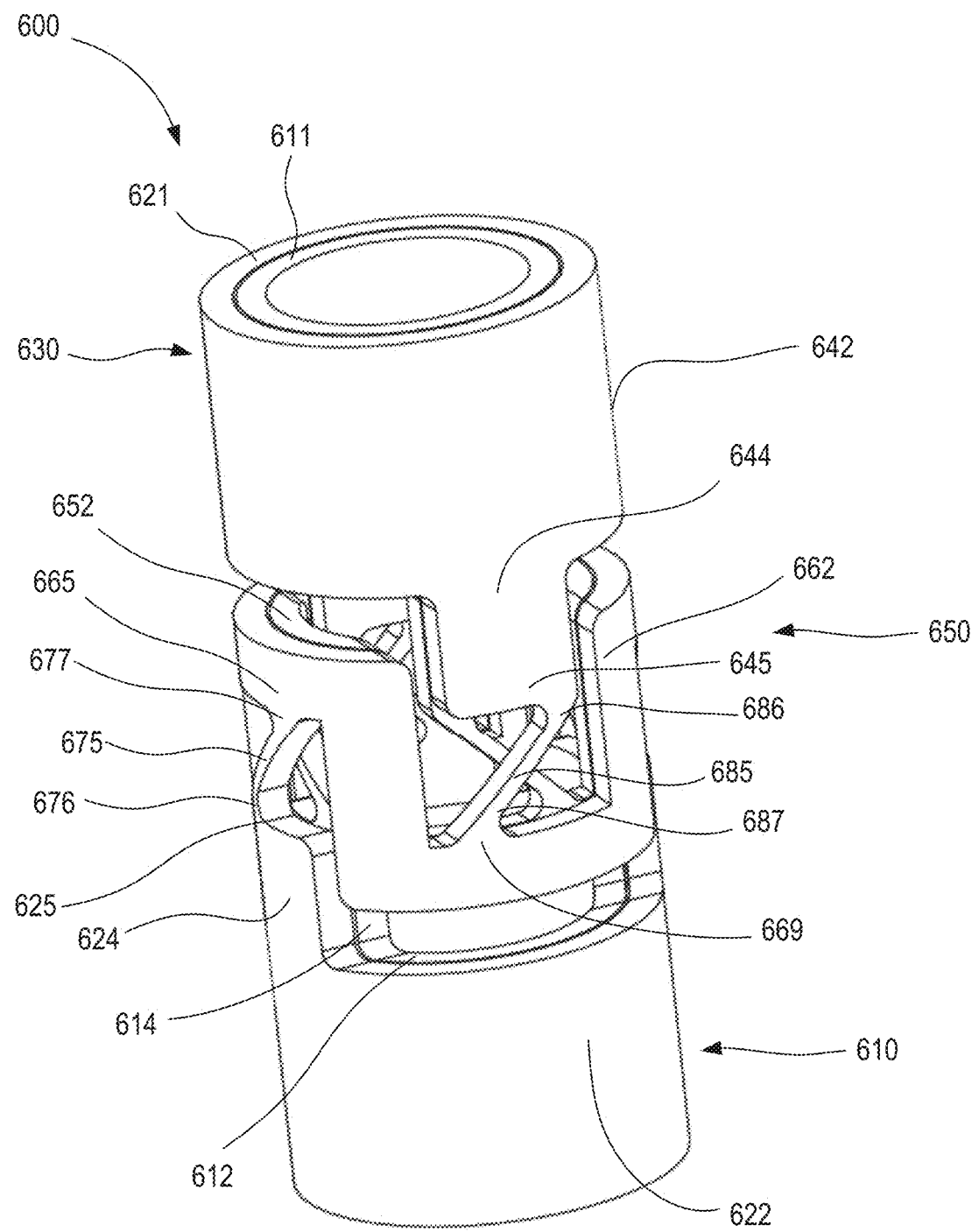
Figure 25:
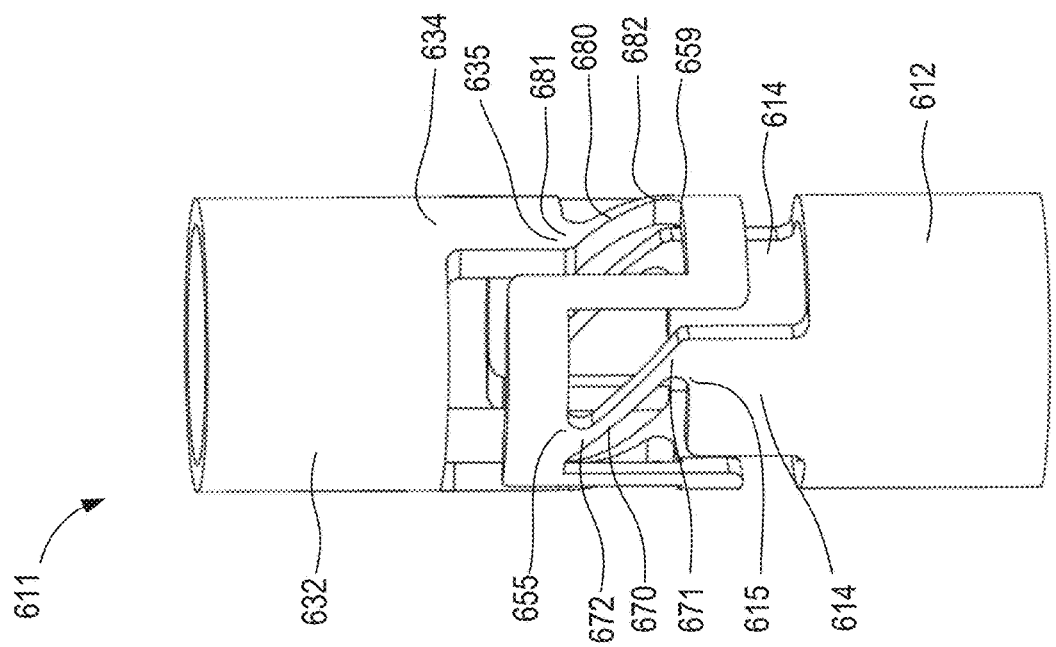
FIGS. 25 and 26 are perspective views of an inner member of the compliant joint mechanism shown in FIGS. 23 and 24.
Figure 26:
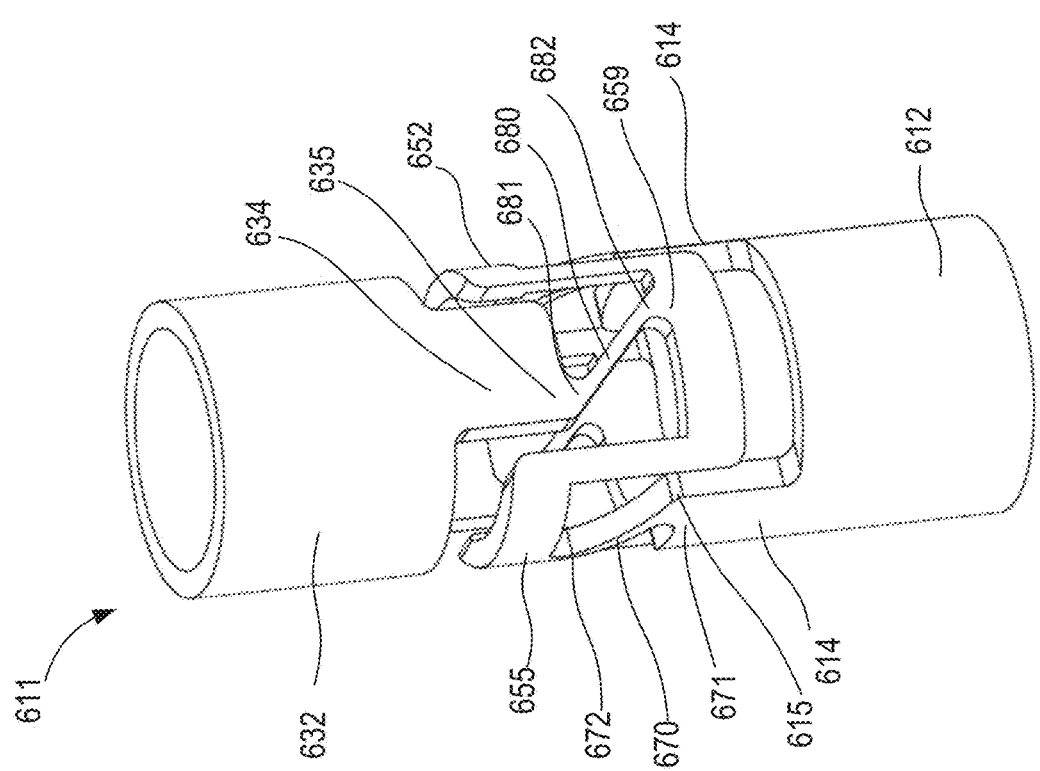
Figure 30:
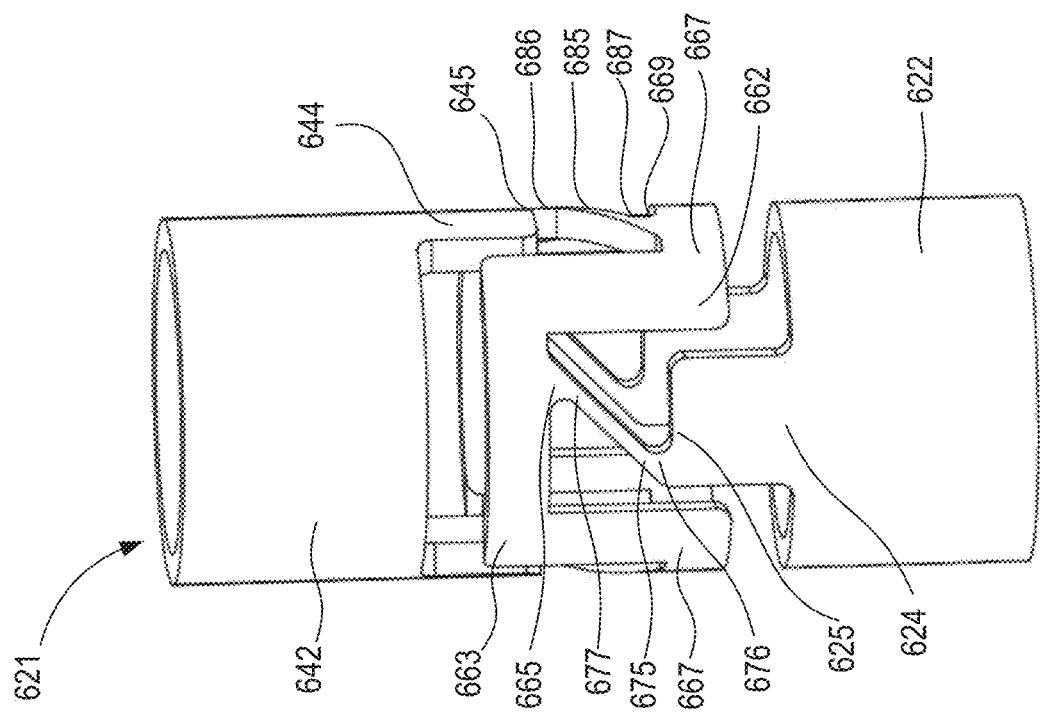
FIGS. 29 and 30 are perspective views of an outer member of the compliant joint mechanism shown in FIGS. 23 and 24.
Figure 29:
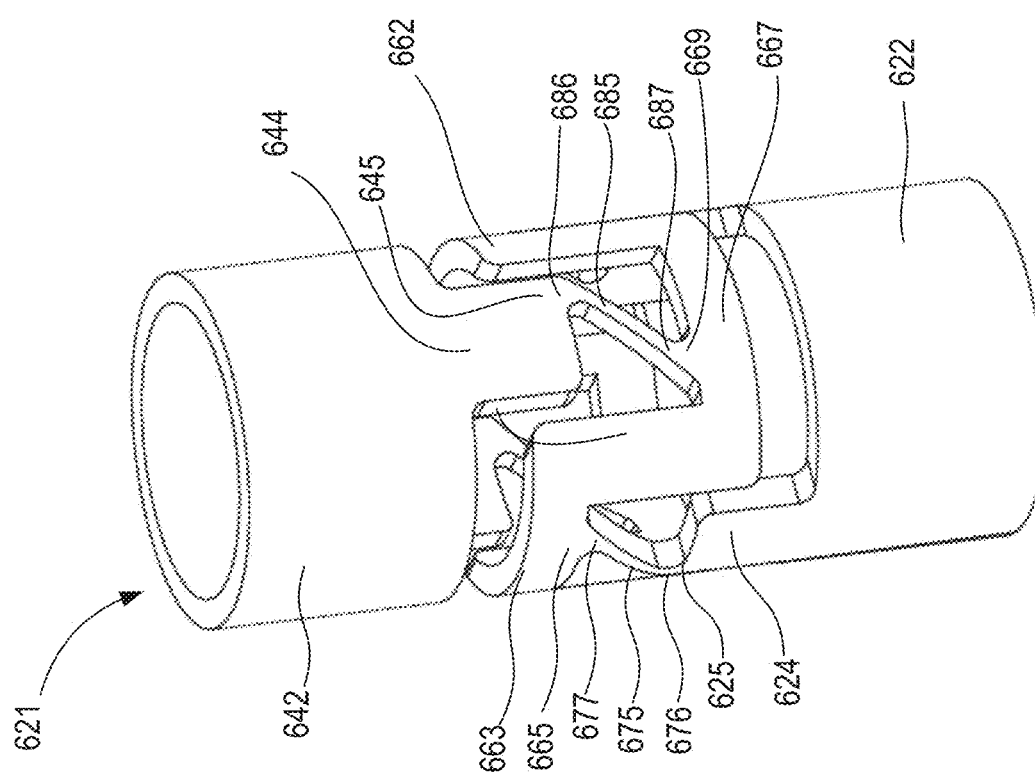

The joint assembly 600 is constructed from an inner cylinder 611 (FIGS. 25-28) and an outer cylinder 621 (FIGS. 29-32). As described in more detail below, the first joint member 610 includes a first end portion 612 of the inner cylinder 611 and a first end portion 622 of the outer cylinder 621. The second joint member 630 includes a second end portion 632 of the inner cylinder 611 and a second end portion 642 of the outer cylinder 621. The third joint member 650 includes a central portion 652 of the inner cylinder 611 and a central portion 662 of the outer cylinder 621. In this manner, when the inner cylinder 611 is disposed within (and coupled to) the outer cylinder 621, as shown in FIGS. 23 and 24, the corresponding portions of the inner cylinder 611 and the outer cylinder 621 form the first joint member 610, the second joint member 630, and the third joint member 650, which are coupled together by the series of flexures (specifically, the first flexures 670, the second flexures 675, the third flexures 680, and the fourth flexures 685.

Referring to FIGS. 25-28, the inner cylinder 611 includes the first end portion 612, the second end portion 632, and the central portion 652. The first flexures 670 (which are circumferentially opposed from each other; i.e., 180 degrees apart) are coupled between the first end portion 612 and the central portion 652. The third flexures 680 (which are circumferentially opposed from each other; i.e., 180 degrees apart) are coupled between the second end portion 632 and the central portion 652. More specifically, each of the third flexures 680 are spaced 90 degrees from each of the first flexures 670. The inner cylinder 611 defines a first axis $AL_1$ (see FIG. 23) that is a longitudinal center line of the inner cylinder 611. Similarly stated, the first axis $AL_1$ is along the center points of the circular cross-sections of the inner cylinder 611. The first end portion 612 includes a pair of connection protrusions 614 each having a connection surface 615. The connection protrusions 614 extend towards and within an opening defined by the central portion 652. In this manner, as described herein, the central portion 652 defines a zig-zag or dogleg shape. The connection surface 615 defines a plane 613 (represented by the dashed lines in FIGS. 27 and 28) that is substantially normal to the first axis $AL_1$. Either of the connection surface 615 or the connection protrusion 614 can have any suitable properties to couple the first end portion 612 to the first flexures 670.

Each of the connection protrusion 614 can be coupled to the corresponding first flexure 670 in any suitable manner. For example, in some embodiments, the connection surface 615 can be a surface (i.e., a connection surface) to which the first flexure 670 is joined (e.g., via welding, adhesive, or the like). In other embodiments, the connection protrusions 614 can include a recess, a fastener, or any other suitable fastening mechanism to which the first flexures 670 are fastened. In yet other embodiments, the connection protrusions 614 can be monolithically formed (i.e., can be integrally formed with) the first flexures 670. For example, in some embodiments, the inner cylinder 611 can be monolithically formed according to the method 10 shown and described herein.

The second end portion 632 includes a pair of connection protrusions 634 each having a connection surface 635. The connection protrusions 634 extend towards and within an opening defined by the central portion 652. In this manner, the central portion 652 defines a zig-zag or dogleg shape. The connection surface 635 defines a plane 633 (represented by the dashed lines in FIGS. 27 and 28) that is substantially normal to the first axis $AL_1$. Either of the connection surface 635 or the connection protrusion 634 can have any suitable properties to couple the second end portion 632 to the third flexures 680. For example, in some embodiments, the connection surfaces 635 are surfaces to which the third flexures 680 are joined (e.g., via welding, adhesive, or the like). In other embodiments, the connection protrusions 634 can include a recess, a fastener, or any other suitable fastening mechanism. In yet other embodiments, the connection protrusions 634 can be monolithically formed (i.e., can be integrally formed with) the third flexures 680.

The central portion 652 includes a first pair of connection members 655 and a second pair of connection members 659. The connection members 655 are circumferentially opposed from each other; i.e., each of the connection members 655 are 180 degrees apart. Similarly, the connection members 659 are circumferentially opposed from each other; i.e., each of the connection members 659 are 180 degrees apart. Thus, each connection member 655 is spaced 90 degrees from each connection member 659. Moreover, the first pair of connection members 655 is at a different location along the first axis $AL_1$, thus forming a zig-zag or dogleg shape. The circumferentially offset shape of the central portion 652 produces the openings within which the connection protrusions 614 and the connection protrusions 634 are disposed.

Each of the first connection members 655 includes a connection surface 653 that defines a plane (represented by the dashed lines in FIGS. 27 and 28) that is substantially normal to the first axis $AL_1$. In some embodiments, the connection surface plane 653 is coplanar with the connection surface plane 633 of the second end portion 632. In this manner, the plane (or point) at which the third flexures 680 are coupled to the second end portion 632 is at the same location along the first axis $AL_1$ as the plane (or point) at which the first flexures 670 are coupled to the central portion 652. This arrangement facilitates the two axes of rotation ($P_1$ and $P_2$, discussed below) intersecting each other. Either of the connection surface 653 or the connection members 655 can have any suitable properties to couple the central portion 652 to the first flexures 670. For example, in some embodiments, the connection surfaces 653 are surfaces to which the first flexures 670 are joined (e.g., via welding, adhesive, or the like). In other embodiments, the connection members 655 can include a recess, a fastener, or any other suitable fastening mechanism. In yet other embodiments, the connection members 655 can be monolithically formed (i.e., can be integrally formed with) the first flexures 670.

Each of the second connection members 659 includes a connection surface 657 that defines a plane (represented by the dashed lines in FIGS. 27 and 28) that is substantially normal to the first axis $AL_1$. In some embodiments, the connection surface plane 657 is coplanar with the connection surface plane 613 of the first end portion 612. In this manner, the plane (or point) at which the first flexures 670 are coupled to the first end portion 632 is at the same location along the first axis $AL_1$ as the plane (or point) at which the third flexures 680 are coupled to the central portion 652. This arrangement facilitates the two axes of rotation ($P_1$ and $P_2$, discussed below) intersecting each other. Either of the connection surface 657 or the connection members 659 can have any suitable properties to couple the central portion 652 to the third flexures 680. For example, in some embodiments, the connection surfaces 657 are surfaces to which the third flexures 680 are joined (e.g., via welding, adhesive, or the like). In other embodiments, the connection members 659 can include a recess, a fastener, or any other suitable fastening mechanism. In yet other embodiments, the connection members 659 can be monolithically formed (i.e., can be integrally formed with) the third flexures 680.

Referring to FIGS. 29-32, the outer cylinder 621 includes the first end portion 622, the second end portion 642, and the central portion 662. The second flexures 675 (which are circumferentially opposed from each other; i.e., 180 degrees apart) are coupled between the first end portion 622 and the central portion 662. The fourth flexures 685 (which are circumferentially opposed from each other; i.e., 180 degrees apart) are coupled between the second end portion 642 and the central portion 662. More specifically, each of the fourth flexures 685 are spaced 90 degrees from each of the second flexures 675. The outer cylinder 621 defines a second axis $AL_2$ (see FIG. 23) that is a longitudinal center line of the outer cylinder 621. Similarly stated, the second axis $AL_2$ is along the center points of the circular cross-sections of the outer cylinder 621. The first end portion 622 includes a pair of connection protrusions 624 each having a connection surface 625. The connection protrusions 624 extend towards and within an opening defined by the central portion 662. In this manner, as described herein, the central portion 662 defines a zig-zag or dogleg shape. The connection surface 625 defines a plane 623 (represented by the dashed lines in FIGS. 31 and 32) that is substantially normal to the second axis $AL_2$. Either of the connection surface 625 or the connection protrusion 624 can have any suitable properties to couple the first end portion 622 to the second flexures 675.

Each of the connection protrusions 624 can be coupled to the corresponding second flexure 675 in any suitable manner. For example, in some embodiments, the connection surface 625 can be a surface (i.e., a connection surface) to which the second flexure 675 is joined (e.g., via welding, adhesive, or the like). In other embodiments, the connection protrusions 624 can include a recess, a fastener, or any other suitable fastening mechanism to which the second flexures 675 are fastened. In yet other embodiments, the connection protrusions 624 can be monolithically formed (i.e., can be integrally formed with) the second flexures 675. For example, in some embodiments, the outer cylinder 621 can be monolithically formed according to the method 10 shown and described herein.

The second end portion 642 includes a pair of connection protrusions 644 each having a connection surface 645. The connection protrusions 644 extend towards and within an opening defined by the central portion 652. In this manner, the central portion 652 defines a zig-zag or dogleg shape. The connection surface 645 defines a plane (represented by the dashed lines in FIGS. 31 and 32) that is substantially normal to the second axis $AL_2$. Either of the connection surface 645 or the connection protrusion 644 can have any suitable properties to couple the second end portion 642 to the fourth flexures 685. For example, in some embodiments, the connection surfaces 645 are surfaces to which the fourth flexures 685 are joined (e.g., via welding, adhesive, or the like). In other embodiments, the connection protrusions 644 can include a recess, a fastener, or any other suitable fastening mechanism. In yet other embodiments, the connection protrusions 644 can be monolithically formed (i.e., can be integrally formed with) the fourth flexures 685.

The central portion 662 includes a first pair of connection members 665 and a second pair of connection members 669. The connection members 665 are circumferentially opposed from each other; i.e., each of the connection members 665 are 180 degrees apart. The connection members 669 are circumferentially opposed from each other; i.e., each of the connection members 669 are 180 degrees apart. Thus, each connection member 665 is spaced 90 degrees from each connection member 669. Moreover, the first pair of connection members 665 is at a different location along the second axis $AL_2$, thus forming a zig-zag or dogleg shape. The circumferentially offset shape of the central portion 662 produces the openings within which the connection protrusions 624 and the connection protrusions 644 are disposed.

Each of the first connection members 665 includes a connection surface 663 that defines a plane (represented by the dashed lines in FIGS. 31 and 32) that is substantially normal to the second axis $AL_2$. In some embodiments, the connection surface plane 663 is coplanar with the connection surface plane 643 of the second end portion 642. In this manner, the plane (or point) at which the fourth flexures 685 are coupled to the second end portion 642 is at the same location along the second axis $AL_2$ as the plane (or point) at which the second flexures 675 are coupled to the central portion 662. This arrangement facilitates the two axes of rotation ($P_1$ and $P_2$, discussed below) intersecting each other. Either of the connection surface 663 or the connection members 665 can have any suitable properties to couple the central portion 662 to the second flexures 675. For example, in some embodiments, the connection surfaces 663 are surfaces to which the second flexures 675 are joined (e.g., via welding, adhesive, or the like). In other embodiments, the connection members 665 can include a recess, a fastener, or any other suitable fastening mechanism. In yet other embodiments, the connection members 665 can be monolithically formed (i.e., can be integrally formed with) the second flexures 675.

Each of the second connection members 669 includes a connection surface 667 that defines a plane (represented by the dashed lines in FIGS. 31 and 32) that is substantially normal to the second axis $AL_2$. In some embodiments, the connection surface plane 667 is coplanar with the connection surface plane 623 of the first end portion 622. In this manner, the plane (or point) at which the second flexures 675 are coupled to the first end portion 622 is at the same location along the second axis $AL_2$ as the plane (or point) at which the fourth flexures 685 are coupled to the central portion 662. This arrangement facilitates the two axes of rotation ($P_1$ and $P_2$, discussed below) intersecting each other.

Either of the connection surface 667 or the connection members 669 can have any suitable properties to couple the central portion 662 to the fourth flexures 685. For example, in some embodiments, the connection surfaces 667 are surfaces to which the fourth flexures 685 are joined (e.g., via welding, adhesive, or the like). In other embodiments, the connection members 669 can include a recess, a fastener, or any other suitable fastening mechanism. In yet other embodiments, the connection members 669 can be monolithically formed (i.e., can be integrally formed with) the fourth flexures 685.

In use, the first flexures 670, the second flexure 675, the third flexures 680, and the fourth flexures 685 each deform elastically when the second joint member 630 moves relative to the first joint member 610. Similarly stated, the flexures deform elastically when the first joint member 610 and the second joint member 630 move between various configurations. Thus, the flexures are resilient members that store energy from an actuation force and releases the energy when the actuation force is removed, thus allowing the joint assembly 600 to repeatedly be moved between the various configurations.

When the joint assembly 600 transitions from the first configuration to the second configuration, the second joint member 630 rotates relative to the first joint member 610, as shown by the arrow EE in FIG. 23. In particular, the second joint member 630 rotates relative to the first joint member 610 about a first axis of rotation (also referred to as a pivot axis), indicated by $P_1$. The first axis of rotation $P_1$ can be approximated as the axis at which the first flexures 670 cross the second flexures 675 when the joint assembly 600 is in the first configuration. As shown in FIG. 23, the first axis $AL_1$ and the second axis $AL_2$ each intersect, and are substantially normal to, the first axis of rotation $P_1$. Moreover, in some embodiments the lengths of these flexures are substantially equal. In such embodiments, the first axis of rotation $P_1$ can be approximated as being at a substantially constant location relative to the first joint member 610 during movement of the second joint member 630. In other embodiments, however, a joint assembly can be configured such that the first axis of rotation $P_1$ is spaced apart from an axis at which the flexures cross, or the first axis of rotation $P_1$ translates when the joint assembly transitions from the first configuration to the second configuration.

When the joint assembly 600 transitions from the first configuration to a third configuration, the second joint member 630 rotates relative to the first joint member 610, as shown by the arrow FF in FIG. 23. In particular, the second joint member 630 rotates relative to the first joint member 610 about a second axis of rotation (also referred to as a pivot axis), indicated by $P_2$. The second axis of rotation $P_2$ can be approximated as the axis at which the third flexures 680 cross the fourth flexures 685 when the joint assembly 600 is in the first configuration. As shown in FIG. 23, the first axis $AL_1$ and the second axis $AL_2$ each intersect, and are substantially normal to, the second axis of rotation $P_2$. Moreover, in some embodiments the lengths of these flexures are substantially equal. In such embodiments, the second axis of rotation $P_2$ can be approximated as being at a substantially constant location relative to the first joint member 610 during movement of the second joint member 630. In other embodiments, however, a joint assembly can be configured such that the second axis of rotation $P_2$ is spaced apart from an axis at which the flexures cross, or the second axis of rotation $P_2$ translates when the joint assembly transitions from the first configuration to the second configuration.

As shown in FIG. 23, the first axis of rotation $P_1$ is normal to, and intersects the second axis of rotation $P_2$. In this manner, the joint assembly can rotate with two degrees of freedom (i.e., rotation in the direction EE and also in the direction FF). Moreover, the offset (or zig-zag) nature of the third (or central) joint member 650 allows the independent motion about the first axis of rotation $P_1$ and the second axis of rotation $P_2$ without binding.

Although not shown in FIGS. 23 and 24, the force to move the second joint member 630 relative to the first joint member 610 (referred to as the actuation force) can be applied to any suitable portion of the joint assembly 600 by any suitable mechanism. For example, in some embodiments, the second joint member 630 can include an engagement portion that receives the actuation force to transition the joint assembly 600 between the various configurations. In some embodiments, the actuation force can be applied via a flexible cable or a rigid rod at a fixed point on the second joint member 630. In other embodiments, the actuation force can be applied via a flexible cable or a rigid rod at multiple points on the second joint member 630. Moreover, the hollow, cylindrical shape of the joint assembly 600 allows the actuation members (e.g., rods, cables, or the like) to be disposed within the inner cylinder 611 of the joint assembly 600. In this manner, the outer surface of the joint assembly 600 can be devoid of moving cables, external rods, or other actuation members that can cause an increased size.

Although the joint assembly 600 is not shown as including any alignment notches (similar to the notches 417 or 437), in other embodiments, either the inner cylinder 611 or the outer cylinder 621 (or both) can include an alignment feature to facilitate circumferential alignment.

Any of the flexures, joint members, inner cylinders or outer cylinders described herein can be constructed from any suitable material to produce the desired flexibility, resilience, and durability during operation. For example, in some embodiments, any of the joint assemblies described herein can be fabricated from stainless steel, titanium, metallic glass, and the nickel titanium alloy, Nitinol®. Nitinol® (also referred to as NiTi) includes nearly equal atomic percentages of nickel and titanium. NiTi can exhibit the superelastic effect and is therefore suitable for use in the compliant mechanisms described herein due to the large strains that it can undergo before yielding. Flexures constructed from NiTi can reach strains of between about 6% and about 8% with very small material set. Conversely, steels generally reach strains on the order of less than 1% before yielding.

To evaluate various materials and flexure designs, finite element modeling was conducted for three different cylindrical, cross-axis flexure joint assembly designs. The general designs were similar to the prototype joint assembly 700 shown above in FIGS. 17-19 (i.e., a baseline design without contact surfaces). The dimensions of the joint assemblies modeled are provided in Table 2 (IC represents the inner cylinder dimensions, and OC represents the outer cylinder dimensions).

Figure 33:
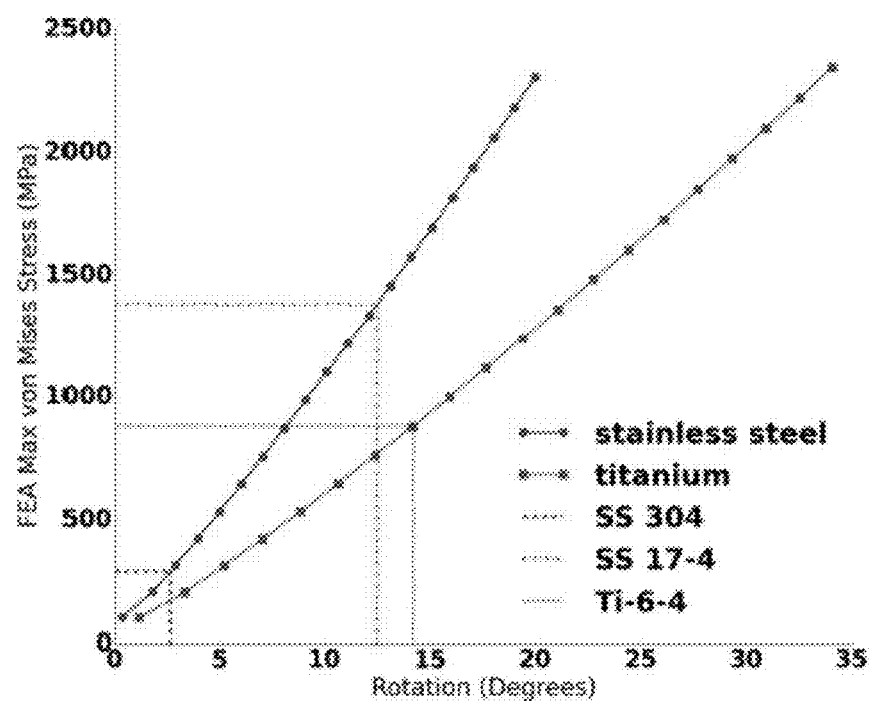
FIG. 33 is a graph showing the maximum von Mises stress as a function of rotation for a joint assembly according to an embodiment.

FIG. 33. The plot in FIG. 33 also includes the yield strength for each of the three alloys considered.

Although the modeling for the joint assembly having a 3 mm nominal size produced angular deflection ranges below 30 degrees, in other embodiments, any of the joint assemblies described herein can be constructed of materials suitable to achieve any desired angular deflection range. For example, in some embodiments, any of the joint assemblies described herein can have an angular deflection range of within ±30 degrees, ±45 degrees, ±60 degrees, ±75 degrees, ±90 degrees, or greater than ±90 degrees. Specifically, to improve the rotation range for the joint assemblies described herein, such joint assemblies can be constructed from NiTi.

Specifically, in such embodiments, the NiTi alloy can be chosen so that it is superelastic at room temperature and above. The superelasticity of NiTi is due to the austenite-martensite phase transformation that occurs when the alloy is mechanically stressed beyond a certain point. NiTi can be strained beyond 6 percent without plastically deforming in many situations, while most steels will typically yield at strains of less than 1 percent. This superelastic behavior enables a greater range of motion when compared to linear elastic materials for a given mechanism geometry.

One consideration in considering the material selection is that NiTi has a nonlinear stress-strain curve with hysteresis. Due to the nonlinear stress-strain response of NiTi, the yield strength is not well defined. Thus, strain is often used as a measure for relative comparisons between designs. For a maximum material strain of 4 percent, the assembly is predicted to undergo 100,000 cycles before failure. A mechanism with 6 percent maximum strain should undergo about 100 cycles before failure.

To evaluate the effect of NiTi on the angular range of various joint assemblies, a finite element analysis was conducted. The material property values for NiTi used are provided in Table 3. The modulus of elasticity of the austenite phase, E, was determined from experimental data. All other values were taken from the literature where $\mu$ is Poisson's ratio, $\sigma^{AS}_S$ is the starting stress value of the forward phase transformation, $\sigma^{AS}_F$ is the final stress value of the forward phase transformation, $\sigma^{SA}_S$ is the starting stress value of the reverse phase transformation, $\sigma^{SA}_F$ is the final stress value of the reverse phase transformation, $\varepsilon_L$ is the maximum residual strain, and $\alpha$ is the material response ratio between tension and compression.

TABLE 2

Joint Assembly Dimensions

| Parameter | 3 mm design | | 5 mm design | | 8 mm design | |
| --- | --- | --- | --- | --- | --- | --- |
| | IC | OC | IC | OC | IC | OC |
| Outer diameter, OD (mm) | 2.374 | 3.001 | 4.798 | 5.499 | 6.998 | 7.998 |
| Inner diameter, ID (mm) | 1.944 | 2.533 | 4.041 | 4.900 | 6.099 | 7.323 |
| Wall thickness, WT (mm) | 0.215 | 0.234 | 0.378 | 0.300 | 0.450 | 0.338 |
| Flexure angle, FA (deg) | 45 | 45 | 45 | 45 | 45 | 45 |
| Flexure thickness, FT (mm) | 0.125 | 0.125 | 0.220 | 0.220 | 0.261 | 0.261 |
| Flexure length, FL (mm) | 2.749 | 2.749 | 5.715 | 5.715 | 8.625 | 8.625 |

Finite element analysis of a 3 mm diameter stainless steel cylindrical, cross-axis flexure joint assembly showed a maximum elastic deflection of ±2.6 degrees for SS304 and ±12.5 degrees for SS17-4. Modeling for a 3 mm cylindrical, cross-axis flexure joint assembly constructed from Ti-6-4 titanium resulted in a maximum elastic deflection of ±14.2 degrees. Results for stainless steel and titanium are shown in

TABLE 3

Material Properties for NiTi (for FE Modeling)

| Property | Value | Property | Value |
| --- | --- | --- | --- |
| E (GPa) | 21.38 | $\sigma^{SA}_S$ (MPa) | 185.5 |
| $\mu$ | 0.3 | $\sigma^{SA}_F$ (MPa) | 112.6 |

TABLE 3-continued

Material Properties for NiTi (for FE Modeling)

| Property | Value | Property | Value |
|---|---|---|---|
| $\sigma^{AS}_S$ (MPa) | 339.0 | $\varepsilon_L$ | 0.048 |
| $\sigma^{AS}_F$ (MPa) | 40.95 | $\alpha$ | 0 |

Figure 34A:
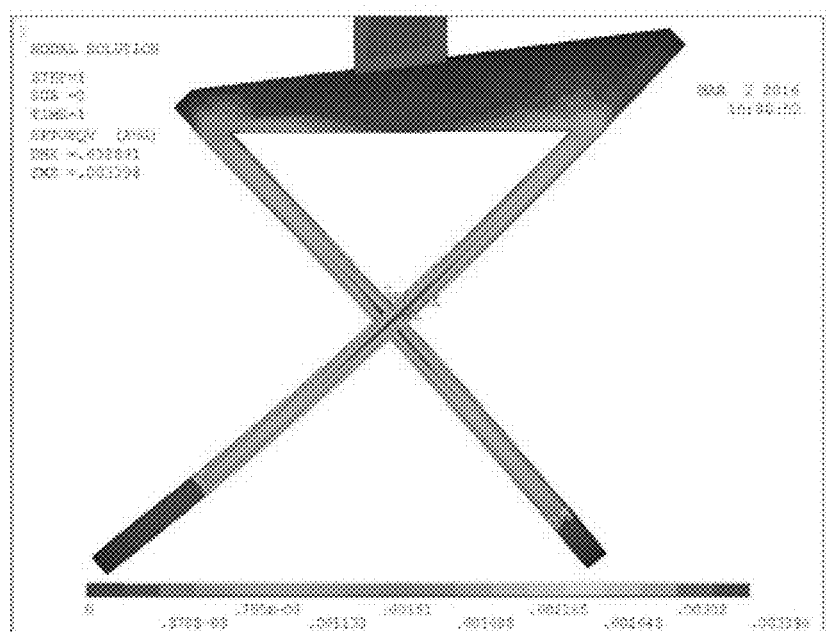
FIG. 34A is a plot of a finite element analysis of a joint assembly according to an embodiment in an undeflected state.
Figure 34B:
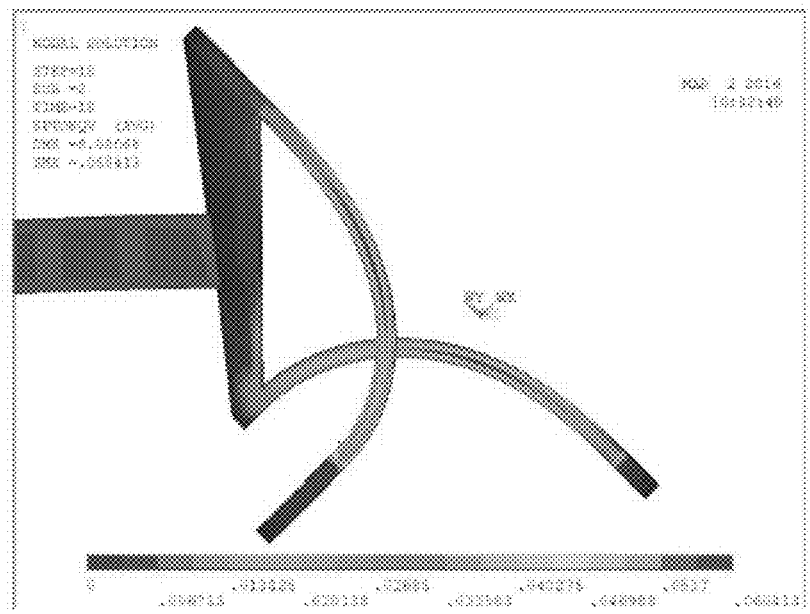
FIGS. 34B and 34C are plots of a finite element analysis of the joint assembly shown in FIG. 34A deflected to about 86 degrees.
Figure 34C:
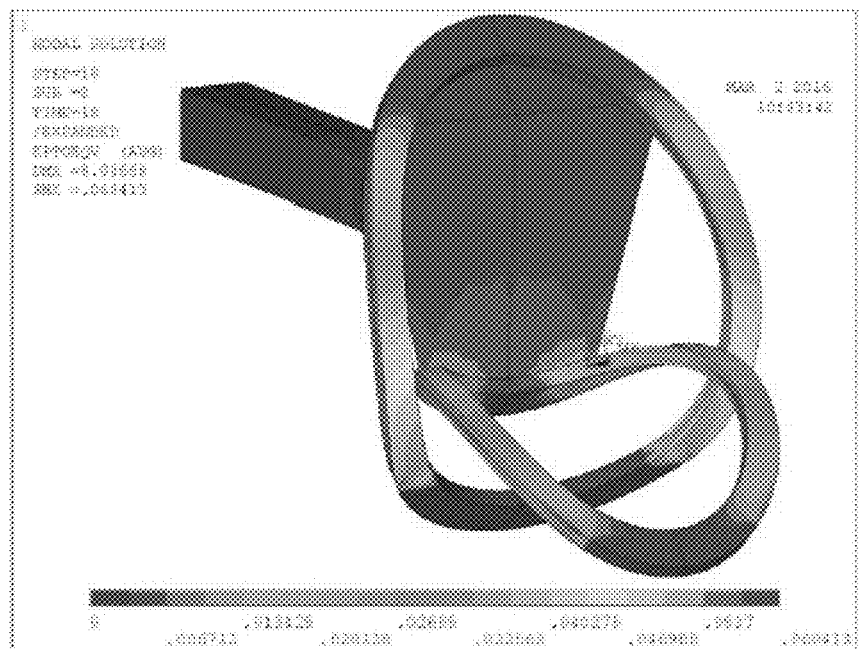
Figure 35:
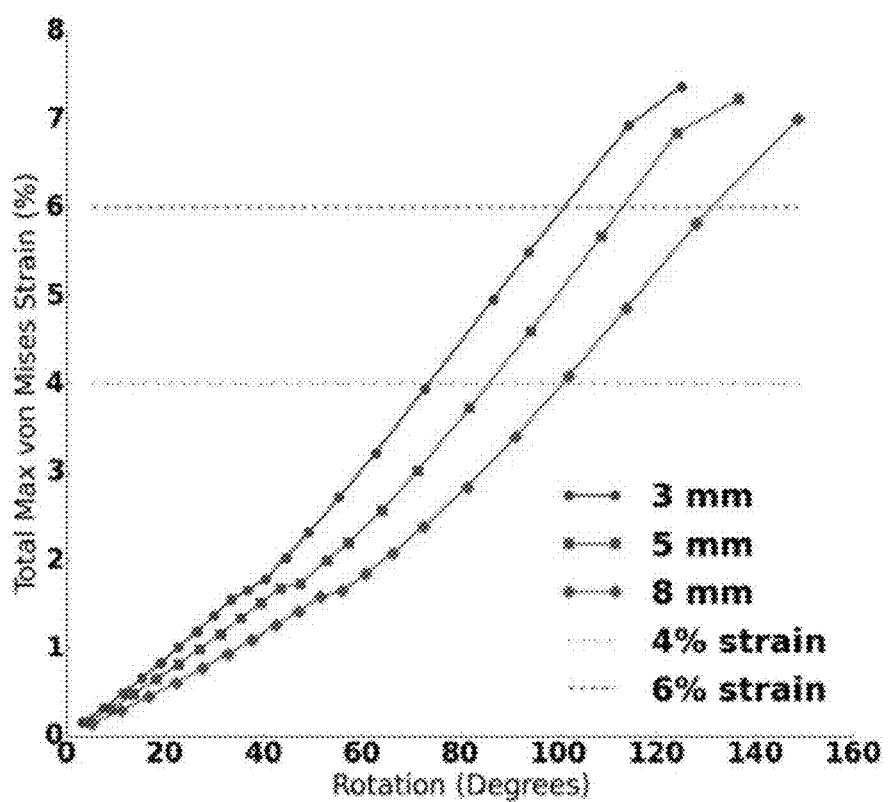
FIG. 35 is a graph showing the maximum von Mises strain as a function of rotation for the joint assembly modeled in FIGS. 34A-34C.
Figure 36:
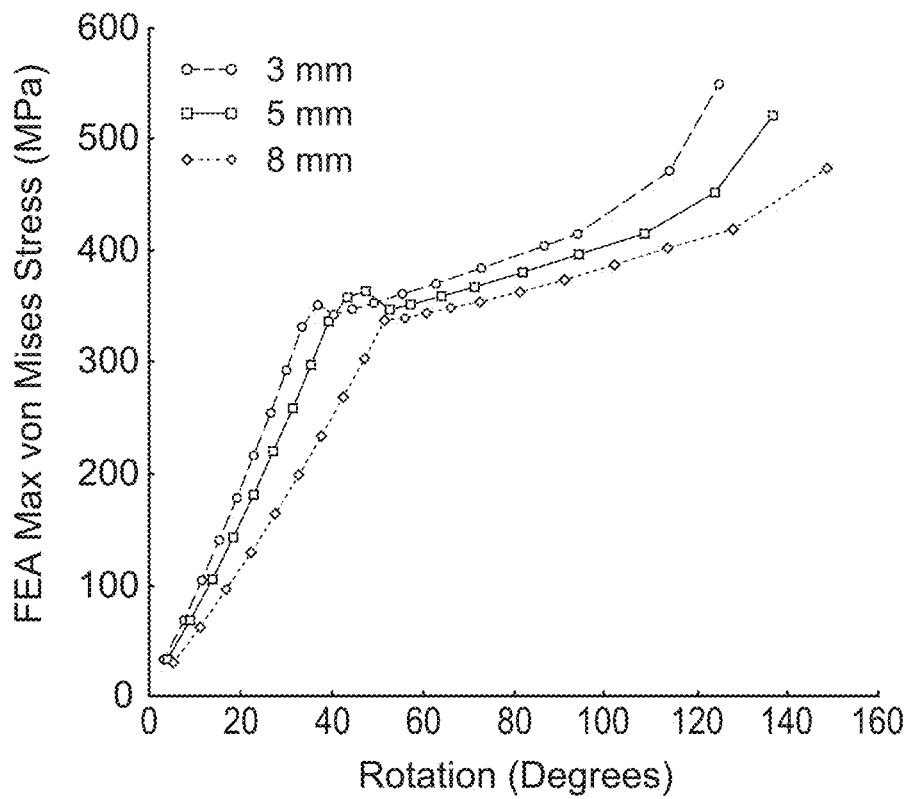
FIG. 36 is a graph showing the maximum von Mises stress as a function of rotation for the joint assembly modeled in FIGS. 34A-34C.
Figure 37:
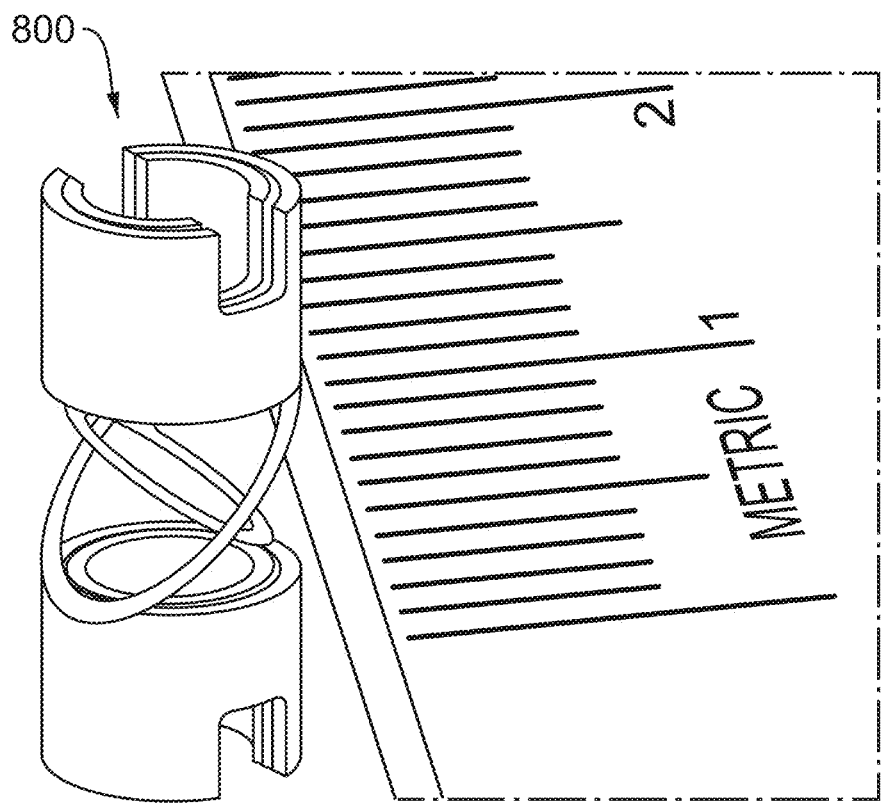
FIGS. 37-40 are photographs of a prototype compliant joint assembly, according to an embodiment.
Figure 38:
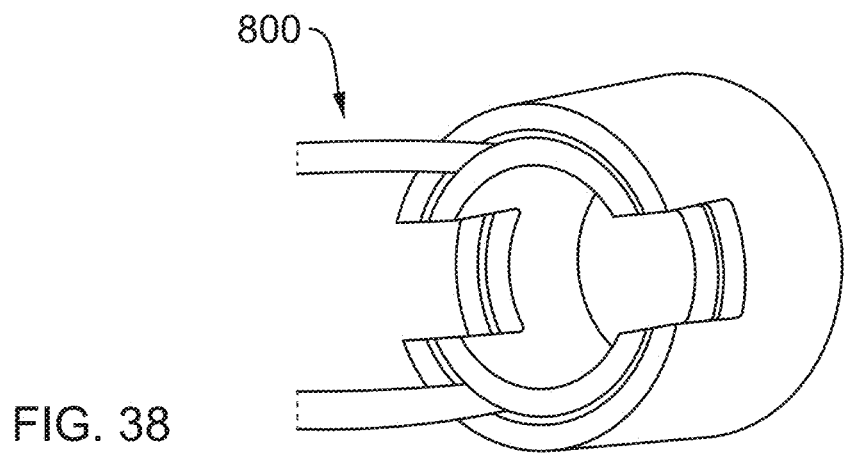
Figure 39:
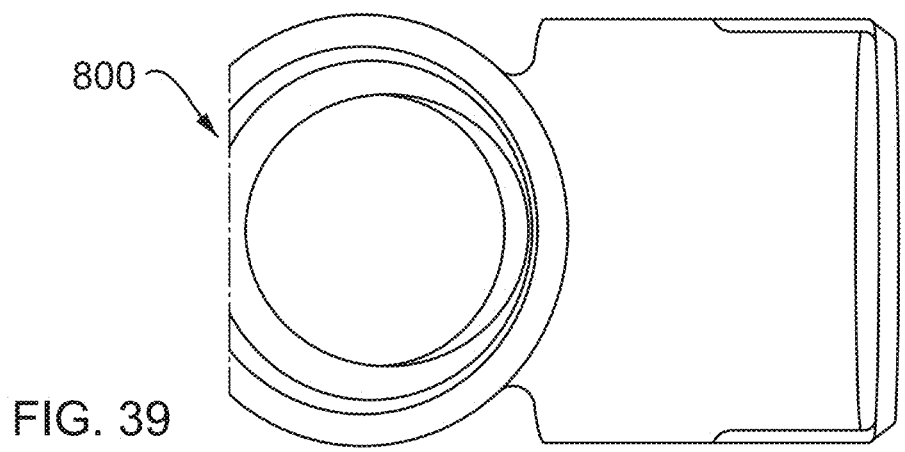
Figure 40:
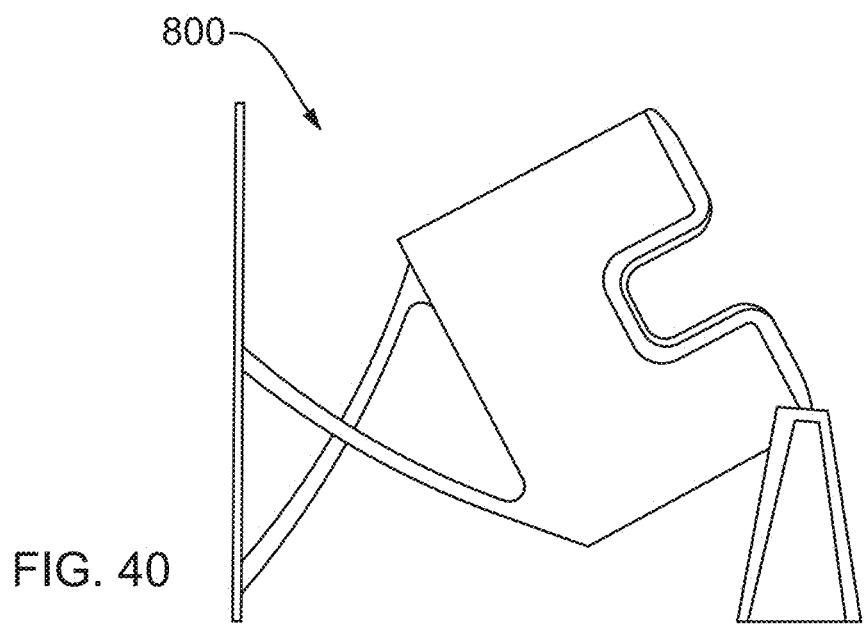

The finite element (FE) model was used to compare the relative performance of the cylindrical, cross-axis flexure joint assembly at three nominal instrument diameters: 3, 5, and 8 mm using the dimensions in Table 2. FIGS. 34A-34C show a representative example of 3 mm joint assembly with strain contours. FIG. 35 is a plot showing the total (elastic+transformation) von Mises strain as a function of angular rotation for each size. Note that FIG. 35 also includes lines representing 4 percent strain and 6 percent strain, which as described above, can be correlated to an expected number of cycles before failure. FIG. 36 is a plot of the maximum von Mises stress developed in the flexures as a function of the angle of rotation.

In addition to modeling the performance of a joint assembly constructed from NiTi, physical prototypes of the 3 mm design (with dimensions as provided in Table 2) were constructed. FIGS. 37-40 are photographs of a joint assembly 800 constructed from NiTi. The joint assembly 800 was manufactured using hollow NiTi cylinders from Minitubes using a wire EDM with a 0.254 mm (0.01 in) kerf width. The flexure lengths of the actual prototypes differed from model dimensions due to fillets that were added to reduce stress concentrations. The actual flexure lengths for the inner and outer flexures were 2.551 mm and 2.547 mm, respectively.

Figure 41:
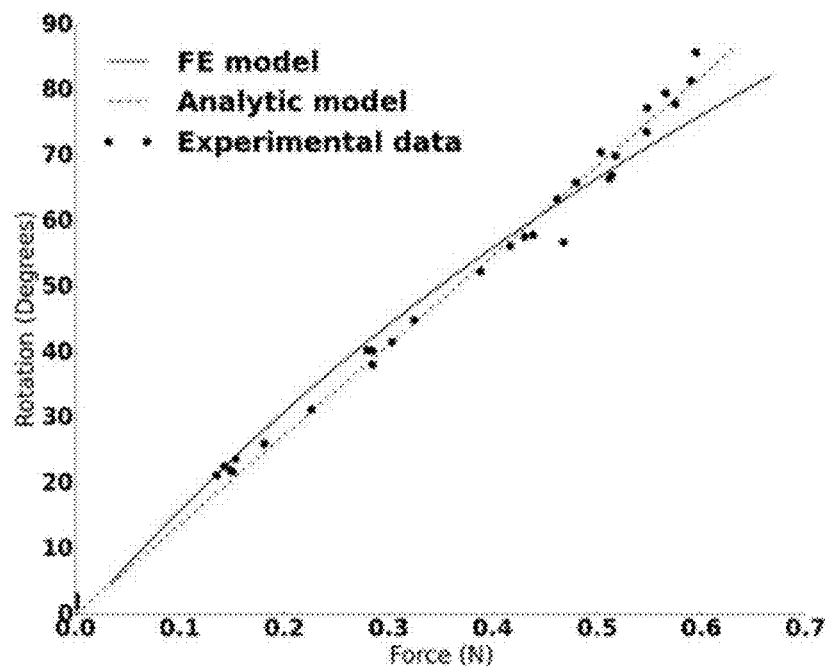
FIG. 41 is a graph showing the angle of rotation as a function of the input force the joint assembly shown in FIGS. 37-40.

The joint assembly 800 was tested using a custom test fixture with a Futek 4.45 N (1 lb) load cell to measure the force required to deflect the assembly. The test fixture was designed to apply a follower force on the rotating end of the mechanism. The joint assembly 800 was test up to an angular deflection of about 85 degrees. FIG. 41 is a plot of the test results compared with both the finite element model results and the analytical analysis. These data suggest a linear relationship between the input force and rotation of the mechanism. Using a least squares linear fit with an intercept at zero, the slope, θ/F, was calculated.

The approximate modulus of elasticity was calculated using the slope and the model for the assembly stiffness, K, where:

$$K = \frac{K_\theta EI}{2l} \quad \text{Eq. (7)}$$

Using a pseudo-rigid-body model and approximating joint assembly as a pin joint, the relationship between the angular deflection of the joint and the applied moment is $$\theta = \frac{M}{2K} \quad \text{Eq. (8)}$$

Rearranging for the modulus of elasticity, E, the equation becomes:

$$E = \frac{Frl}{\theta K A_\theta I_{avg}} \quad \text{Eq. (9)}$$

Where F is the applied force, r is the perpendicular distance from the pseudo-pivot to the applied force (the moment arm), l is the flexure length, and $I_{avg}$ is the average second moment of area of the flexure. An average value of I was used because the flexure widths of the inner and outer flexures are slightly different, as well as the fact that the flexure width changes as a function of position along the flexure due to the elliptical geometry. Note that the original model assumes a pure moment is applied to the joint assembly. For this analysis, an approximate moment was applied as a force at a distance.

Figure 42:
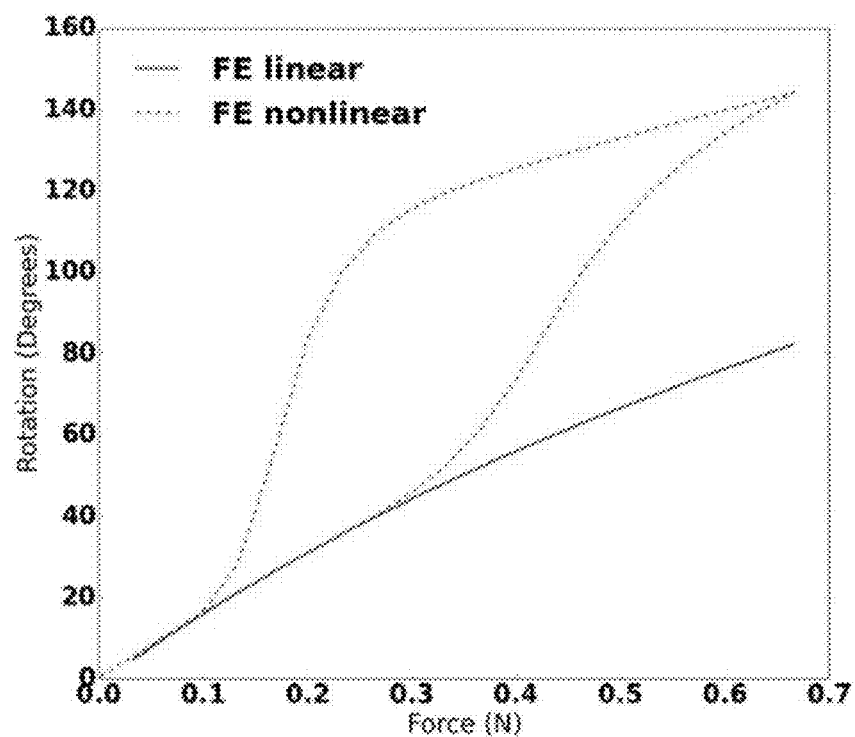
FIG. 42 is a graph showing the angle of rotation as a function of the input force the joint assembly shown in FIGS. 37-40, showing both linear and non-linear properties.

The modulus of elasticity calculated using experimental data and Eq. (9) was used in the FE model. As noted above, the comparison is plotted in FIG. 41. FIG. 42 shows a plot of the FE model with linear and nonlinear material properties. This shows that the nonlinear material properties of NiTi may enable larger rotations for a given input force. Note that nonlinear material properties of NiTi cause hysteresis in the force-deflection relationship.

Figure 43:
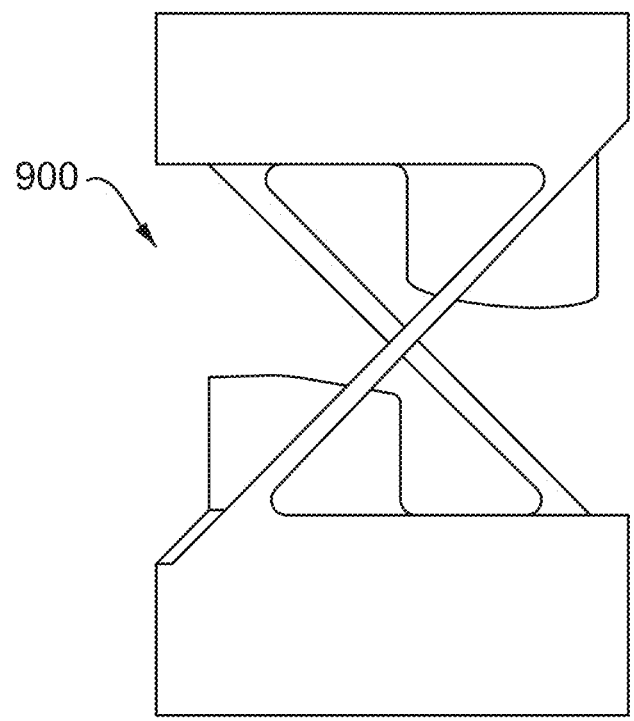
FIGS. 43-44 are photographs of a prototype compliant joint assembly, according to an embodiment.
Figure 44:
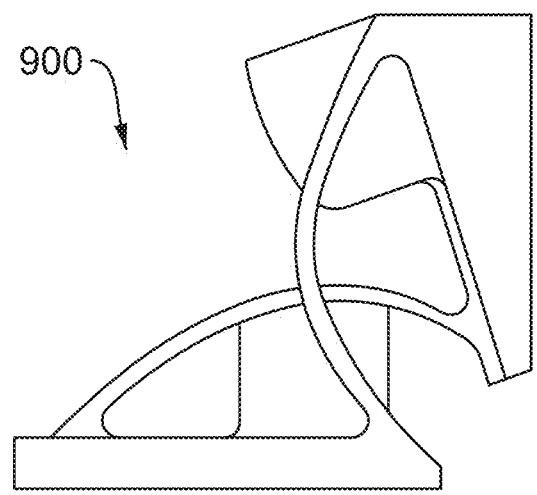

Although the above modeling and experimental data is described in connection with the physical prototype 800, additional physical prototypes including the contact (or cam) surfaces described herein were constructed. FIGS. 43 and 44 are photographs of a joint assembly 900 that includes contact surfaces on the inner cylinder of the joint assembly (similar to that shown and described above with reference to joint assembly 400).

Any of the joint assemblies described herein can be fabricated according to any suitable method. For example, in some embodiments, a cylindrical, cross-axis joint assembly (e.g., the joint assemblies 400, 500, or 600) can be fabricated from tubular stock using a variety of material-removal methods, including laser-cutting, wire-EDM, waterjet, and traditional machining. In other embodiments, however, a cylindrical member, such as any of the inner cylinders or outer cylinders disclosed herein can be fabricated by first removing the material from a planar material sheet, and then later rolling (or forming) the material into a tubular member. For example, as shown in FIG. 45, If one cylindrical member of a joint assembly, such as the inner cylinder 411, the outer cylinder 421 or any of the cylindrical members described herein, were "unrolled" onto a plane the resulting geometry becomes two offset curves with three areas of material "cutout."

Figure 45:
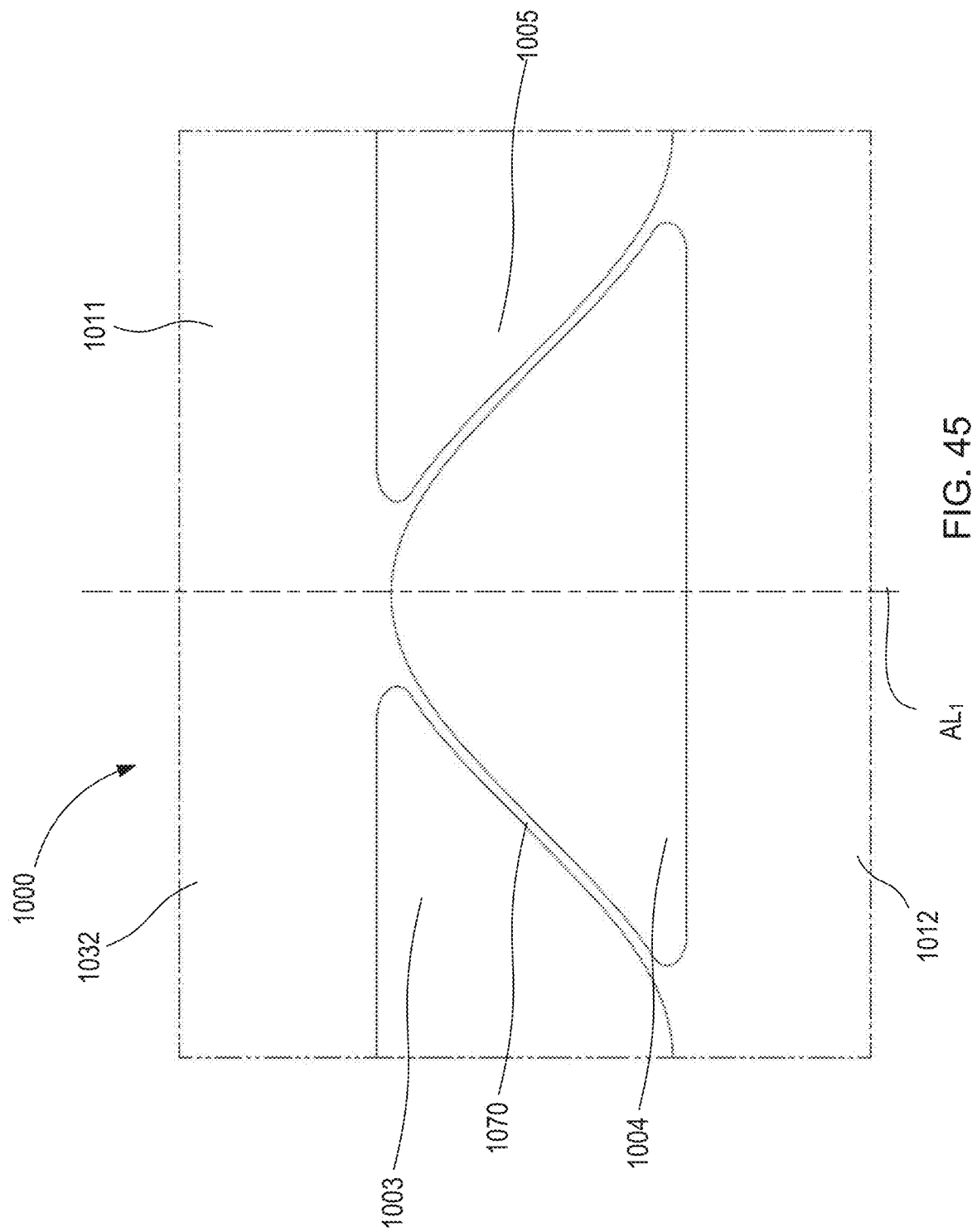
FIG. 45 is a schematic illustration of a portion of a joint assembly being constructed using a method according to an embodiment.

Specifically, FIG. 45 shows a planar material sheet 1000 from which a cylinder member 1011 can be fabricated. When fabricated, the cylinder member 1011 includes a first end portion 1012, a second end portion 1032, and a flexure 1070 coupling the first end portion 1012 and the second end portion 1032. To fabricate the cylinder member 1011, material is removed from three sections, identified as section 1003, section 1004, and section 1005 of the material sheet 1000 to define the shape and size of the flexure 1070. To produce the elliptical shaped flexure 1070 (which is similar to the flexure 470 and 475 shown above) two offset sinusoid curves are defined on the planar material sheet 1000.

The mathematical equation for an elliptic cross-section created by a plane intersecting a cylinder is provided in Eq. 10 below, where h=r(tan β) and β is the angle between a plane orthogonal to the cylinder axis and the flexure.

$$u(x) = h \sin \frac{x}{r} \quad \text{Eq. (10)}$$

-continued $$\frac{du(x)}{dx} = \frac{h}{r} \cos \frac{x}{r} \quad \text{Eq. (11)}$$

$$x^* = x_p \pm \frac{t}{2} \cos \theta \quad \text{Eq. (12)}$$

$$y^* = y_p \pm \frac{t}{2} \sin \theta \quad \text{Eq. (13)}$$

The offset curves that define the thickness of the flexure 1070 are calculated via the analytic derivative of the sinusoid function, shown in Eq. 11 above. The negative inverse of the derivative is then taken to find the slope perpendicular to the tangent line at each particular point along the primary curve. The location of the offset at each point is provided by Eq. 12 and 13, where x* and y* are the offset distances from the point (x,y).

After the material is removed from section 1003, section 1004, and section 1005, the planar sheet 1000 can then be rolled about the axis $AL_1$ to form the cylinder member 1011.

Figure 46:
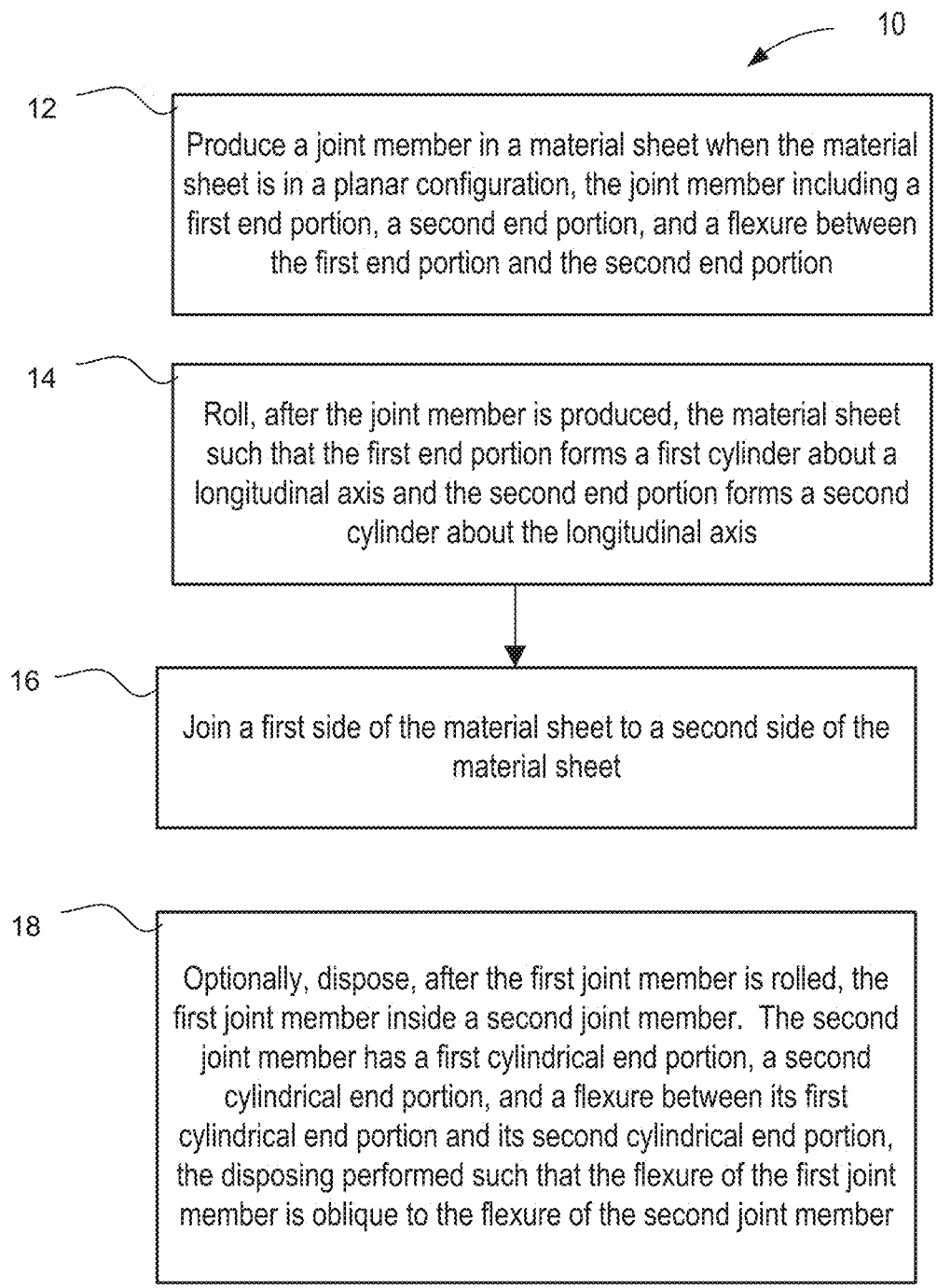
FIG. 46 is a flow diagram of a method of fabricating a joint assembly according to an embodiment.

FIG. 46 is a flow chart of a method 10 of producing a cylindrical portion of a joint assembly, according to an embodiment. The method 10 can be performed to produce any of the devices, joint assemblies, or components thereof described herein. The method 10 includes producing a joint member in a material sheet when the material sheet is in a planar configuration, at 12. The joint member can be any of the joint members or cylinders described herein, and includes a first end portion, a second end portion, and a flexure between the first end portion and the second end portion. In some embodiments, the producing includes removing material from between the first end portion and the second end portion to define a shape of the flexure. The material can be removed by any suitable method, such as, for example, electrical discharge machining (EDM), laser-cutting, waterjet, and traditional machining.

The method further includes rolling, after the producing, the material sheet such that the first end portion forms a first cylinder about a longitudinal axis and the second end portion forms a second cylinder about the longitudinal axis, at 14. A first side of the material sheet is then joined to a second side of the material sheet, at 16. In some embodiments, joint member is a first cylindrical joint member, and the method 10 optionally includes disposing, after the rolling, the first joint member inside a second joint member, at 18. The second joint member has a first cylindrical end portion, a second cylindrical end portion, and a flexure between the first cylindrical end portion of the second joint member and a second cylindrical end portion of the second joint member. The disposing is performed such that the flexure of the first joint member is oblique to the flexure of the second joint member.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the tool members can be constructed from any material, such as medical grade stainless steel, nickel alloys, titanium alloys or the like. Further, any of the joint assemblies or components described herein can be constructed from multiple pieces that are later joined together. For example, in some embodiments, a joint member can be constructed by joining together separately constructed components (e.g., the lateral arm, the spool, the longitudinal arm). In other embodiments, however, any of the joint assemblies or components described herein (e.g., the inner or outer cylinders) can be monolithically constructed.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

For example, in some embodiments, any of the joint assemblies described herein can include one or more contact surfaces, similar to the contact surface 416 shown and described above. For example, although the joint assembly 600 is not shown as including a contact surface against which the flexures engage, in some embodiments, the joint assembly 600 can include one or more contact surfaces.

What is claimed is:
1. An apparatus, comprising:
a first joint member having a first end portion, a second end portion, and a first flexure between the first end portion and the second end portion of the first joint member, the first end portion of the first joint member having a first cylindrical portion and a contact surface, the second end portion of the first joint member having a second cylindrical portion; and
a second joint member having a first end portion, a second end portion, and a second flexure between the first end portion and the second end portion of the second joint member, the first end portion of the second joint member having a third cylindrical portion, the second end portion of the second joint member having a fourth cylindrical portion,
the first joint member being disposed inside the second joint member such that the first cylindrical portion of the first joint member is at least partially disposed within the third cylindrical portion of the second joint member and the contact surface of the first end portion of the first joint member extends beyond the third cylindrical portion of the second joint member, and
the first flexure is configured to transition between a first configuration and a second configuration when the second end portion of the first joint member rotates relative to the first end portion of the first joint member about a first axis of rotation,
a central portion of the first flexure is spaced apart from the contact surface when the first flexure is in the first configuration, and
the central portion of the first flexure is in contact with the contact surface when the first flexure is in the second configuration.
2. The apparatus of claim 1, wherein:
the first flexure is configured to deform elastically when the second end portion of the first joint member rotates relative to the first end portion of the first joint member about the first axis of rotation; and
the second flexure is configured to deform elastically when the second end portion of the second joint member rotates relative to the first end portion of the second joint member about the first axis of rotation.
3. The apparatus of claim 2, wherein:
the contact surface is a first contact surface;

the first end portion of the second joint member having a second contact surface;

the second flexure configured to transition between a first configuration and a second configuration when the second end portion of the second joint member rotates relative to the first end portion of the second joint member about the first axis of rotation, a central portion of the second flexure is spaced apart from the second contact surface when the second flexure is in the first configuration, and the central portion of the second flexure is in contact with the second contact surface when the second flexure is in the second configuration.

4. The apparatus of claim 1, wherein:

the first cylindrical portion of the first joint member defines a first notch, the third cylindrical portion of the second joint member defines a second notch, the first notch substantially aligned with the second notch.

5. The apparatus of claim 1, wherein:

the first cylindrical portion of the first joint member has a first center axis and the second cylindrical portion of the first joint member has a second center axis, the second center axis is noncoaxial with the first center axis when the second end portion of the first joint member rotates relative to the first end portion of the first joint member about the first axis of rotation.

6. The apparatus of claim 1, wherein:

the first end portion of the first joint member, the first flexure, and the second end portion of the first joint member are monolithically formed; and the first end portion of the second joint member, the second flexure, and the second end portion of the second joint member are monolithically formed.

7. The apparatus of claim 1, wherein:

at least a portion of the contact surface is curved.

8. The apparatus of claim 1, wherein:

the first joint member and the second joint member define a longitudinal axis when the first joint member and the second joint member are collectively in a first configuration; and the first axis of rotation is normal to the longitudinal axis.

9. A method of producing the apparatus of claim 1, where the first joint member is produced in a material sheet when the material sheet is in a planar configuration, characterized by the method comprising:

rolling the material sheet such that the first end portion of the first joint member forms the first cylindrical portion about a longitudinal axis and the second end portion of the first joint member forms the second cylindrical portion about the longitudinal axis;

joining, after the rolling, a first side of the material sheet to a second side of the material sheet;

disposing, after the rolling, the first joint member inside the second joint member; and the disposing is performed such that the first flexure of the first joint member is oblique to the second flexure of the second joint member;

wherein the first joint member and the second joint member define a pivot axis about which the second end portion of the first joint member rotates relative to the first end portion of the first joint member when the first flexure of the first joint member and the second flexure of the second joint member deform elastically.

\* \* \* \* \*